(12) United States Patent
Enya et al.

(10) Patent No.: US 10,144,931 B2
(45) Date of Patent: Dec. 4, 2018

(54) ANTISENSE NUCLEIC ACIDS

(71) Applicants: NIPPON SHINYAKU CO., LTD., Kyoto-shi, Kyoto (JP); NATIONAL CENTER OF NEUROLOGY AND PSYCHIATRY, Kodaira-shi, Tokyo (JP)

(72) Inventors: Yukiko Enya, Ibaraki (JP); Yuichiro Tone, Ibaraki (JP); Shin'ichi Takeda, Tokyo (JP); Yoshitsugu Aoki, Tokyo (JP)

(73) Assignees: NIPPON SHINYAKU CO., LTD., Kyoto-shi, Kyoto (JP); NATIONAL CENTER OF NEUROLOGY AND PSYCHIATRY, Kodaira-shi, Tokyo (JP)

( * ) Notice: Subject to any disclaimer, the term of this patent is extended or adjusted under 35 U.S.C. 154(b) by 0 days.

(21) Appl. No.: 15/759,267

(22) PCT Filed: Sep. 15, 2016

(86) PCT No.: PCT/JP2016/077305
§ 371 (c)(1),
(2) Date: Mar. 12, 2018

(87) PCT Pub. No.: WO2017/047707
PCT Pub. Date: Mar. 23, 2017

(65) Prior Publication Data
US 2018/0265866 A1    Sep. 20, 2018

(30) Foreign Application Priority Data

Sep. 15, 2015 (JP) .................................. 2015-182145

(51) Int. Cl.
| C07H 21/02 | (2006.01) |
| C07H 21/04 | (2006.01) |
| A61K 31/70 | (2006.01) |
| C12N 15/113 | (2010.01) |
| C12N 5/00 | (2006.01) |

(52) U.S. Cl.
CPC ........ *C12N 15/113* (2013.01); *C12N 2310/11* (2013.01); *C12N 2310/313* (2013.01); *C12N 2310/314* (2013.01); *C12N 2310/321* (2013.01); *C12N 2310/3233* (2013.01)

(58) Field of Classification Search
None
See application file for complete search history.

(56) References Cited

U.S. PATENT DOCUMENTS

| 8,871,918 B2 | 10/2014 | Sazani et al. |
| 9,078,911 B2 | 7/2015 | Lu |
| 9,890,381 B2 | 2/2018 | Watanabe et al. |
| 2010/0168212 A1 | 7/2010 | Popplewell et al. |

FOREIGN PATENT DOCUMENTS

| JP | 2012-506697 A | 3/2012 |
| JP | 2012-506703 A | 3/2012 |
| JP | 2014-0507143 A | 3/2014 |
| JP | 2015-522275 A | 8/2015 |
| WO | WO-2004/048570 A1 | 6/2004 |
| WO | WO-2006/000057 A1 | 1/2006 |
| WO | WO-2007/135105 A1 | 11/2007 |
| WO | WO-2009/139630 A2 | 11/2009 |
| WO | WO-2010/048586 A1 | 4/2010 |
| WO | WO-2010/050801 A1 | 5/2010 |
| WO | WO-2011/057350 A1 | 5/2011 |
| WO | WO-2013/100190 A1 | 7/2013 |
| WO | WO-2014/007620 A2 | 1/2014 |

OTHER PUBLICATIONS

English translation of International Search Report dated Nov. 8, 2016 from International application No. PCT/JP2016/077305.
English translation of Written Opinion dated Nov. 8, 2016 from International patent application No. PCT/JP2016/077305.
Aartsma-Rus, Annemieke et al., "Targeted exon skipping as a potential gene correction therapy for Duchenne muscular dystrophy," Neuromuscular Disorders, 2002, vol. 12, pp. 71-77.
Wilton, Steve et al., "Antisense Oligonucleotide-induced Exon Skipping Across the Human Dystrophin Gene Transcript," Molecular Therapy, Jul. 2007, vol. 15, No. 7, pp. 1288-1296.

*Primary Examiner* — Sean McGarry
(74) *Attorney, Agent, or Firm* — Drinker Biddle & Reath LLP

(57) ABSTRACT

The present invention provides an oligomer which allows exon 45 skipping in the human dystrophin gene.

19 Claims, 13 Drawing Sheets

Specification includes a Sequence Listing.

SEQUENCE LISTING

```
<160> NUMBER OF SEQ ID NOS: 146

<210> SEQ ID NO 1
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 1
gctcaggtcg gattgacatt                                                    20

<210> SEQ ID NO 2
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 2
gggcaactct tccaccagta                                                    20

<210> SEQ ID NO 3
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 3
tacaggaact ccaggatggc                                                    20

<210> SEQ ID NO 4
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 4
gaatgcaact ggggaagaaa taa                                                23

<210> SEQ ID NO 5
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 5
atctgcggtg gcaggaggtc tgc                                                23

<210> SEQ ID NO 6
<211> LENGTH: 26
```

<212> TYPE: DNA
<213> ORGANISM: Artificial
<220> FEATURE:
<223> OTHER INFORMATION: Synthetic Nucleic Acid

<400> SEQUENCE: 6
cattgggcag cggcaaactg ttgtca                                    26

<210> SEQ ID NO 7
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 7
gtttgccgct gcctcctgga gttcct                                    26

<210> SEQ ID NO 8
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 8
gtttgccgct gccctggagt tcct                                      24

<210> SEQ ID NO 9
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 9
cagtttgccg ctgcccatcc tggagttcct                                30

<210> SEQ ID NO 10
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 10
cagtttgccg ctgccctgga gttcct                                    26

<210> SEQ ID NO 11
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 11
ttcttcccca gttgcgccat cctggagttc                                30

<210> SEQ ID NO 12
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 12
cagacctcct gccacgccat cctggagttc                                       30

<210> SEQ ID NO 13
<211> LENGTH: 176
<212> TYPE: DNA
<213> ORGANISM: Homo sapiens

<400> SEQUENCE: 13
gaactccagg atggcattgg gcagcggcaa actgttgtca gaacattgaa tgcaactggg      60
gaagaaataa ttcagcaatc ctcaaaaaca gatgccagta ttctacagga aaaattggga    120
agcctgaatc tgcggtggca ggaggtctgc aaacagctgt cagacagaaa aaagag        176

<210> SEQ ID NO 14
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 14
ttgccgctgc ccacatcctg gagttc                                           26

<210> SEQ ID NO 15
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 15
gccgctgccc acatcctgga gttcct                                           26

<210> SEQ ID NO 16
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 16
ccgctgccca atgtcctgga gttcct                                           26

<210> SEQ ID NO 17
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 17
ttgccgctgc ccatcctgga gttcct                                           26

<210> SEQ ID NO 18
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 18
tttgccgctg ccatcctgga gttcct                                           26

<210> SEQ ID NO 19
<211> LENGTH: 24

```
<212> TYPE: DNA
<213> ORGANISM: Artificial
<220> FEATURE:
<223> OTHER INFORMATION: Synthetic Nucleic Acid

<400> SEQUENCE: 19
tttgccgctg cctcctggag ttcc                                          24

<210> SEQ ID NO 20
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 20
tgccgctgcc cgccatcctg gagttc                                        26

<210> SEQ ID NO 21
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 21
gtttgccgct gccatcctgg agttc                                         25

<210> SEQ ID NO 22
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 22
cagtttgccg ctgctggagt tcct                                          24

<210> SEQ ID NO 23
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 23
acagtttgcc gctctggagt tcct                                          24

<210> SEQ ID NO 24
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 24
cagtttgccg ctgccggagt tcct                                          24

<210> SEQ ID NO 25
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 25
```

-continued

```
gtttgccgct gccctggagt tcc                                          23

<210> SEQ ID NO 26
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 26
cagtttgccg ctgccggagt tcctg                                        25

<210> SEQ ID NO 27
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 27
ccgctgccca atgtggagtt cctgt                                        25

<210> SEQ ID NO 28
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 28
cagtttgccg ctgccctgga gttc                                         24

<210> SEQ ID NO 29
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 29
ccgctgccca atctggagtt cct                                          23

<210> SEQ ID NO 30
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 30
cagtttgccg ctgccctgga gttcc                                        25

<210> SEQ ID NO 31
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 31
ttgccgctgc ccactggagt tcct                                         24

<210> SEQ ID NO 32
<211> LENGTH: 26
<212> TYPE: DNA
<213> ORGANISM: Artificial
```

```
<220> FEATURE:
<223> OTHER INFORMATION: Synthetic Nucleic Acid

<400> SEQUENCE: 32
ttgccgctgc ccactggagt tcctgt                                          26

<210> SEQ ID NO 33
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 33
acagtttgcc gcctggagtt cc                                              22

<210> SEQ ID NO 34
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 34
gtttgccgct gc                                                         12

<210> SEQ ID NO 35
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 35
cctggagttc ct                                                         12

<210> SEQ ID NO 36
<211> LENGTH: 10
<212> TYPE: DNA
<213> ORGANISM: Artificial
<220> FEATURE:
<223> OTHER INFORMATION: Synthetic Nucleic Acid

<400> SEQUENCE: 36
tggagttcct                                                            10

<210> SEQ ID NO 37
<211> LENGTH: 16
<212> TYPE: DNA
<213> ORGANISM: Artificial
<220> FEATURE:
<223> OTHER INFORMATION: Synthetic Nucleic Acid

<400> SEQUENCE: 37
cagtttgccg ctgccc                                                     16

<210> SEQ ID NO 38
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 38
tcttccccag ttgccatcct ggagtt                                          26
```

```
<210> SEQ ID NO 39
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 39
agacctcctg ccaccatcct ggagtt                                        26

<210> SEQ ID NO 40
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 40
gacctcctgc caccatcctg gagttc                                        26

<210> SEQ ID NO 41
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 41
tccccagttg cgccatcctg gagttc                                        26

<210> SEQ ID NO 42
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 42
gacctcctgc cgccatcctg gagttc                                        26

<210> SEQ ID NO 43
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 43
cttccccagt tgccatcctg gagttc                                        26

<210> SEQ ID NO 44
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 44
ttccccagtt gcacatcctg gagttc                                        26

<210> SEQ ID NO 45
<211> LENGTH: 26
<212> TYPE: DNA
<213> ORGANISM: Artificial
<220> FEATURE:
<223> OTHER INFORMATION: Synthetic Nucleic Acid
```

<400> SEQUENCE: 45
cctcctgcca ccgcatcctg gagttc                                              26

<210> SEQ ID NO 46
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 46
acctcctgcc acccatcctg gagttc                                              26

<210> SEQ ID NO 47
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 47
tttcttcccc agtcatcctg gagttc                                              26

<210> SEQ ID NO 48
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 48
gcagacctcc tgccatcctg gagttc                                              26

<210> SEQ ID NO 49
<211> LENGTH: 28
<212> TYPE: DNA
<213> ORGANISM: Artificial
<220> FEATURE:
<223> OTHER INFORMATION: Synthetic Nucleic Acid

<400> SEQUENCE: 49
ttcttcccca gttgccatcc tggagttc                                            28

<210> SEQ ID NO 50
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 50
ccccagttgc atctggagtt cct                                                 23

<210> SEQ ID NO 51
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 51
ttcttcccca gttgccctgg agttcc                                              26

<210> SEQ ID NO 52

<211> LENGTH: 28
<212> TYPE: DNA
<213> ORGANISM: Artificial
<220> FEATURE:
<223> OTHER INFORMATION: Synthetic Nucleic Acid

<400> SEQUENCE: 52
cttccccagt tgccatcctg gagttcct                                         28

<210> SEQ ID NO 53
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 53
cagacctcct gccactcctg gagttc                                           26

<210> SEQ ID NO 54
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 54
tgcagacctc ctgcctcctg gagttc                                           26

<210> SEQ ID NO 55
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 55
ctgtttgcag acccatcctg gagttc                                           26

<210> SEQ ID NO 56
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 56
tttgcagacc tcctggagtt cctgta                                           26

<210> SEQ ID NO 57
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 57
cctgccaccg cagatgccat cctggagttc                                       30

<210> SEQ ID NO 58
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 58
acctcctgcc accgcttgcc gctgcccaat                                      30

<210> SEQ ID NO 59
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 59
tcctgtagaa taccatcctg gagttc                                          26

<210> SEQ ID NO 60
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 60
ctcctgccac cgctggcatc tgtttt                                          26

<210> SEQ ID NO 61
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 61
acctcctgcc accgctcttc cccagttgca                                      30

<210> SEQ ID NO 62
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 62
tggcatctgt tttcatcctg gagttc                                          26

<210> SEQ ID NO 63
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 63
ttatttcttc cccagttcct gtaaga                                          26

<210> SEQ ID NO 64
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 64
gcttcccaat gccatcctgg agttcc                                          26

<210> SEQ ID NO 65
<211> LENGTH: 26
<212> TYPE: DNA

<213> ORGANISM: Artificial
<220> FEATURE:
<223> OTHER INFORMATION: Synthetic Nucleic Acid

<400> SEQUENCE: 65
ggcttcccaa tgccatcctg gagttc                                    26

<210> SEQ ID NO 66
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 66
tttctgtctg acagctcctg ccaccgcaga                                30

<210> SEQ ID NO 67
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 67
tcctgccacc gcagagagga ttgctgaatt                                30

<210> SEQ ID NO 68
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 68
tcctgccacc gcagactggc atctgttttt                                30

<210> SEQ ID NO 69
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 69
tcctgccacc gcagattttc ctgtagaata                                30

<210> SEQ ID NO 70
<211> LENGTH: 15
<212> TYPE: DNA
<213> ORGANISM: Artificial
<220> FEATURE:
<223> OTHER INFORMATION: Synthetic Nucleic Acid

<400> SEQUENCE: 70
gccatcctgg agttc                                                15

<210> SEQ ID NO 71
<211> LENGTH: 15
<212> TYPE: DNA
<213> ORGANISM: Artificial
<220> FEATURE:
<223> OTHER INFORMATION: Synthetic Nucleic Acid

<400> SEQUENCE: 71
ttcttcccca gttgc                                                15

<210> SEQ ID NO 72
<211> LENGTH: 15
<212> TYPE: DNA
<213> ORGANISM: Artificial
<220> FEATURE:
<223> OTHER INFORMATION: Synthetic Nucleic Acid

<400> SEQUENCE: 72
cagacctcct gccac                                                  15

<210> SEQ ID NO 73
<211> LENGTH: 13
<212> TYPE: DNA
<213> ORGANISM: Artificial
<220> FEATURE:
<223> OTHER INFORMATION: Synthetic Nucleic Acid

<400> SEQUENCE: 73
tcctggagtt cct                                                    13

<210> SEQ ID NO 74
<211> LENGTH: 13
<212> TYPE: DNA
<213> ORGANISM: Artificial
<220> FEATURE:
<223> OTHER INFORMATION: Synthetic Nucleic Acid

<400> SEQUENCE: 74
gtttgccgct gcc                                                    13

<210> SEQ ID NO 75
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 75
ctcctgccac cgcgccgctg cccaat                                      26

<210> SEQ ID NO 76
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 76
attcaggctt cccttcccca gttgca                                      26

<210> SEQ ID NO 77
<211> LENGTH: 9
<212> TYPE: DNA
<213> ORGANISM: Artificial
<220> FEATURE:
<223> OTHER INFORMATION: Synthetic Nucleic Acid

<400> SEQUENCE: 77 tggagttcc                                                          9

<210> SEQ ID NO 78
<211> LENGTH: 8
<212> TYPE: DNA
<213> ORGANISM: Artificial
<220> FEATURE:

<223> OTHER INFORMATION: Synthetic Nucleic Acid

<400> SEQUENCE: 78 tggagttc  8

<210> SEQ ID NO 79
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 79
cagtttgccg cctggagttc c  21

<210> SEQ ID NO 80
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 80
acagtttgcc gctggagttc ct  22

<210> SEQ ID NO 81
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 81
gtttgccgct gcctggagtt cc  22

<210> SEQ ID NO 82
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 82
aacagtttgc ccctggagtt cc  22

<210> SEQ ID NO 83
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 83
cagtttgccg cctggagttc  20

<210> SEQ ID NO 84
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 84
cagtttgccg ctcctggagt tc  22

```
<210> SEQ ID NO 85
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 85
agtttgccgc tcctggagtt c                                              21

<210> SEQ ID NO 86
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 86
acagtttgcc gctggagttc c                                              21

<210> SEQ ID NO 87
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 87
tgccgctgcc catcctggag ttcc                                           24

<210> SEQ ID NO 88
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 88
ctgccaccgc agccgctgcc caatgc                                         26

<210> SEQ ID NO 89
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 89
uccccaguug cauucgccau ccuggaguuc                                     30

<210> SEQ ID NO 90
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 90
uuauuucuuc cccaggccau ccuggaguuc                                     30

<210> SEQ ID NO 91
<211> LENGTH: 30
<212> TYPE: DNA
<213> ORGANISM: Artificial
<220> FEATURE:
<223> OTHER INFORMATION: Synthetic Nucleic Acid
```

```
<400> SEQUENCE: 91
ccuccugcca ccgcagccau ccuggaguuc                                30

<210> SEQ ID NO 92
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 92
ccuccugcca ccgcacaucc uggaguuccu                                30

<210> SEQ ID NO 93
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 93
cagaccuccu gccaccaucc uggaguuccu                                30

<210> SEQ ID NO 94
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 94
uccccaguug cauuccaucc uggaguuccu                                30

<210> SEQ ID NO 95
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 95
uucuucccca guugccaucc uggaguuccu                                30

<210> SEQ ID NO 96
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 96
uuauuucuuc cccagcaucc uggaguuccu                                30

<210> SEQ ID NO 97
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 97
guuugccgcu gcccacaucc uggaguuccu                                30

<210> SEQ ID NO 98
<211> LENGTH: 30
```

<212> TYPE: DNA
<213> ORGANISM: Artificial
<220> FEATURE:
<223> OTHER INFORMATION: Synthetic Nucleic Acid

<400> SEQUENCE: 98
uuugcagacc uccugcaucc uggaguuccu                                    30

<210> SEQ ID NO 99
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 99
gaccuccugc cacaugccau ccuggaguuc                                    30

<210> SEQ ID NO 100
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 100
cuuccccagu ugcaugccau ccuggaguuc                                    30

<210> SEQ ID NO 101
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 101
uuugcagacc uccuggccau ccuggaguuc                                    30

<210> SEQ ID NO 102
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 102
uuuuccugua gaauacaucc uggaguuccu                                    30

<210> SEQ ID NO 103
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 103
accuccugcc accgcuuucu uccccaguug                                    30

<210> SEQ ID NO 104
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 104
uuuuccugua gaauauugcc gcugcccaau                             30

<210> SEQ ID NO 105
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 105
cugucugaca gcugugccau ccuggaguuc                             30

<210> SEQ ID NO 106
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 106
ggauugcuga auuaugccau ccuggaguuc                             30

<210> SEQ ID NO 107
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 107
uuuuccugua gaauagccau ccuggaguuc                             30

<210> SEQ ID NO 108
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 108
caguugcauu caacauccug gaguuc                                 26

<210> SEQ ID NO 109
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 109
uucuucccca guucauccug gaguuc                                 26

<210> SEQ ID NO 110
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 110
ugaauuauuu cuucauccug gaguuc                                 26

<210> SEQ ID NO 111
<211> LENGTH: 26
<212> TYPE: DNA
<213> ORGANISM: Artificial

```
<220> FEATURE:
<223> OTHER INFORMATION: Synthetic Nucleic Acid

<400> SEQUENCE: 111
caguugcauu caaaaugcca uccugg                                    26

<210> SEQ ID NO 112
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 112
uucuucccca guuaaugcca uccugg                                    26

<210> SEQ ID NO 113
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 113
ugaauuauuu cuuaaugcca uccugg                                    26

<210> SEQ ID NO 114
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 114
gcagauucag gcucauccug gaguuc                                    26

<210> SEQ ID NO 115
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 115
cugccaccgc agacauccug gaguuc                                    26

<210> SEQ ID NO 116
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 116
cagaccuccu gcccauccug gaguuc                                    26

<210> SEQ ID NO 117
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 117
gcagauucag gcuaaugcca uccugg                                    26
```

```
<210> SEQ ID NO 118
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 118
cugccaccgc agaaaugcca uccugg                                          26

<210> SEQ ID NO 119
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 119
uucaggcuuc ccagccgcug cccaau                                          26

<210> SEQ ID NO 120
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 120
accgcagauu caggccgcug cccaau                                          26

<210> SEQ ID NO 121
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 121
cuccugccac cgcgccgcug cccaau                                          26

<210> SEQ ID NO 122
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 122
uucaggcuuc ccaacaacag uuugcc                                          26

<210> SEQ ID NO 123
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 123
accgcagauu cagacaacag uuugcc                                          26

<210> SEQ ID NO 124
<211> LENGTH: 26
<212> TYPE: DNA
<213> ORGANISM: Artificial
<220> FEATURE:
<223> OTHER INFORMATION: Synthetic Nucleic Acid
```

```
<400> SEQUENCE: 124
cuccugccac cgcacaacag uuugcc                                              26

<210> SEQ ID NO 125
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 125
cuucccaauu uuuuccccca guugca                                              26

<210> SEQ ID NO 126
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 126
auucaggcuu cccuuccccca guugca                                             26

<210> SEQ ID NO 127
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 127
accgcagauu caguccccca guugca                                              26

<210> SEQ ID NO 128
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 128
cuucccaauu uuuaauuauu ucuucc                                              26

<210> SEQ ID NO 129
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 129
auucaggcuu cccaauuauu ucuucc                                              26

<210> SEQ ID NO 130
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 130
accgcagauu cagaauuauu ucuucc                                              26

<210> SEQ ID NO 131
```

```
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 131
cuucccaauu uuugauugcu gaauua                                              26

<210> SEQ ID NO 132
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 132
auucaggcuu cccgauugcu gaauua                                              26

<210> SEQ ID NO 133
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 133
accgcagauu caggauugcu gaauua                                              26

<210> SEQ ID NO 134
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 134
uucuucccca guugcaguuc cuguaagaua                                          30

<210> SEQ ID NO 135
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 135
cagaccuccu gccacaguuc cuguaagaua                                          30

<210> SEQ ID NO 136
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 136
ccuguagaau acugggagga uugcugaauu                                          30

<210> SEQ ID NO 137
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 137
```
cuggcaucug uuuuuugcc gcugcccaau                              30

<210> SEQ ID NO 138
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 138
uuucuucccc aguuguugcc gcugcccaau                              30

<210> SEQ ID NO 139
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 139
cuggcaucug uuuuugccau ccuggaguuc                              30

<210> SEQ ID NO 140
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 140
accuccugcc accgccuggc aucuguuuuu                              30

<210> SEQ ID NO 141
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 141
uuuuccugua gaauauuucu uccccaguug                              30

<210> SEQ ID NO 142
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 142
cagaccuccu gccaaugcca uccugg                                  26

<210> SEQ ID NO 143
<211> LENGTH: 16
<212> TYPE: DNA
<213> ORGANISM: Artificial
<220> FEATURE:
<223> OTHER INFORMATION: Synthetic Nucleic Acid

<400> SEQUENCE: 143
aaaaattggg aagcct                                             16

<210> SEQ ID NO 144
<211> LENGTH: 11
<212> TYPE: DNA

```
<213> ORGANISM: Artificial Sequence
<220> FEATURE:
<223> OTHER INFORMATION: synthetic nucleic acid

<400> SEQUENCE: 144
cctggagttc c                                                          11

<210> SEQ ID NO 145
<211> LENGTH: 10
<212> TYPE: DNA
<213> ORGANISM: Artificial Sequence
<220> FEATURE:
<223> OTHER INFORMATION: synthetic nucleic acid

<400> SEQUENCE: 145
cagtttgccg                                                            10

<210> SEQ ID NO 146
<211> LENGTH: 11
<212> TYPE: DNA
<213> ORGANISM: Artificial Sequence
<220> FEATURE:
<223> OTHER INFORMATION: synthetic nucleic acid

<400> SEQUENCE: 146
acagtttgcc g                                                          11
```

ANTISENSE NUCLEIC ACIDS

CROSS REFERENCES TO RELATED APPLICATIONS

This application is the National Stage of International Application No. PCT/JP2016/077305, filed Sep. 15, 2016, and claims benefit of Japanese Application No. 2015-182145, filed on Sep. 15, 2015.

REFERENCE TO A SEQUENCE LISTING

The instant application contains a sequence listing which has been submitted in ASCII format via EFS-Web and is hereby incorporated by reference in its entirety. Said ASCII copy, created on Sep. 15, 2016, is named P248158_Seq_List_4996630.txt and is 27,652 bytes in size.

TECHNICAL FIELD

The present invention relates to an antisense oligomer which allows exon 45 skipping in the human dystrophin gene, and a pharmaceutical composition comprising such an oligomer.

BACKGROUND ART

Duchenne muscular dystrophy (DMD) is an inherited progressive myopathy with the highest incidence which occurs at a frequency of about one in 3,500 live male births. In their infancy, DMD patients show almost the same motor function as in normal humans, but they show signs of muscle weakness around the ages of 4 to 5 years. Then, their muscle weakness progresses to the loss of ambulation until the age of about 12 years and eventually leads to death in their twenties due to heart failure or respiratory failure. DMD is such a sever disease. Currently, there is no effective therapy for DMD, and hence the development of a new therapeutic agent is strongly demanded.

DMD is known to be caused by mutations in the dystrophin gene. The dystrophin gene is located on the X chromosome and is a huge gene consisting of 2.2 million DNA nucleotide pairs. This DNA is transcribed into precursor mRNA and further spliced to remove introns, thereby resulting in mRNA consisting of 79 exons joined together, which is 13,993 bases in length. This mRNA is translated into 3,685 amino acids to produce a dystrophin protein. The dystrophin protein is involved in maintenance of the membrane stability of muscle cells and is required to make muscle cells less prone to breakage. DMD patients have mutations in their dystrophin gene and therefore show almost no expression of a functional dystrophin protein in their muscle cells. For this reason, in the body of DMD patients, muscle cells can no longer retain their structure and an abundance of calcium ions flows into the muscle cells. As a result, a reaction similar to inflammation will occur to promote fibrosis, so that muscle cells are difficult to regenerate.

Becker muscular dystrophy (BMD) is also caused by mutations in the dystrophin gene. As its symptom, muscle weakness is observed, but is usually milder and progresses slower than in DMD, so that BMD develops in adulthood in most cases. Differences in clinical symptoms between DMD and BMD appear to arise from whether mutations disrupt or maintain the amino acid reading frame during translation from dystrophin mRNA into a dystrophin protein (Non-patent Document 1). Namely, DMD patients show almost no expression of a functional dystrophin protein because of having mutations responsible for shifting the amino acid reading frame, whereas in BMD patients, mutations cause deletion of some exons but the amino acid reading frame is maintained, so that a functional albeit incomplete dystrophin protein is produced.

As a therapy for DMD, the exon skipping therapy is promising. This therapy involves modification of splicing to restore the amino acid reading frame in dystrophin mRNA, thereby inducing the expression of a dystrophin protein with partially recovered function (Non-patent Document 2). Amino acid sequence regions targeted by exon skipping are deleted in this therapy. For this reason, a dystrophin protein expressed in this therapy is shorter than the normal protein, but partially retains the function of stabilizing muscle cells because the amino acid reading frame is maintained. It is therefore expected that exon skipping allows DMD to present the same symptoms as seen in BMD which is milder. The exon skipping therapy is now under clinical trial in human DMD patients after animal experiments in mice and dogs.

Exon skipping can be induced by binding of antisense nucleic acids directed against either or both of the 5' and 3' splice sites or against exon internal sequences. An exon is included into mRNA only when its both splice sites are recognized by a spliceosome complex. Thus, exon skipping can be induced when the splice sites are targeted by antisense nucleic acids. Moreover, to induce exon recognition by the splicing machinery, SR proteins rich in serine and arginine would be required to bind to exon splicing enhancers (ESEs); and hence exon skipping can also be induced upon targeting to ESEs.

DMD patients have different mutations in their dystrophin gene, and hence various antisense nucleic acids are required depending on the position and type of gene mutation. There are some reports of an antisense nucleic acid designed to induce exon skipping of a single exon in the dystrophin gene by targeting a single continuous sequence (Patent Documents 1 to 6, as well as Non-patent Documents 1 and 2). In addition, there is a report showing that when two different antisense nucleic acids directed against the same exon in the dystrophin gene are allowed to act in admixture (double targeting), skipping activity may be enhanced as compared to when each antisense nucleic acid is used alone (Patent Document 7).

However, there has been no report showing that connected single-stranded antisense nucleic acids directed against two or more sites in the same exon (i.e., antisense nucleic acid of connected type) show skipping activity.

PRIOR ART DOCUMENTS

Patent Documents

Patent Document 1: WO2004/048570
Patent Document 2: WO2009/139630
Patent Document 3: WO2010/048586
Patent Document 4: US2010/0168212
Patent Document 5: WO2011/057350
Patent Document 6: WO2006/000057
Patent Document 7: WO2007/135105

Non-Patent Documents

Non-patent Document 1: Annemieke Aartsma-Rus et al., (2002) Neuromuscular Disorders 12: S71-S77
Non-patent Document 2: Wilton S. D., et al., Molecular Therapy 2007: 15: p. 1288-96

SUMMARY OF THE INVENTION

Problem to be Solved by the Invention

Under such circumstances as described above, the present invention mainly aims to provide a novel antisense oligomer of connected type which is designed to induce exon skipping by targeting separate two nucleotide sequences in the same exon of the dystrophin gene, and a therapeutic agent for muscular dystrophy comprising such an oligomer.

Means to Solve the Problem

As a result of detailed studies on the technical contents described in the above documents and on the structure of the dystrophin gene, etc., the inventors of the present invention have found that oligomers directed against two separate sites in exon 45 of the human dystrophin gene are connected together and the resulting antisense oligomer can induce skipping of this exon. The inventors of the present invention have completed the present invention on the basis of this finding.

Namely, the present invention is as follows.

[1] An antisense oligomer of 14 to 32 bases in length comprising connected two unit oligomers selected from the group consisting of (a) to (e) shown below, or a pharmaceutically acceptable salt or hydrate thereof, wherein the two unit oligomers are not contiguous to each other or do not overlap with each other:
(a) a unit oligomer consisting of a nucleotide sequence complementary to a nucleotide sequence consisting of contiguous 7 to 16 bases selected from a nucleotide sequence located at positions –5 to 15 from the 5'-terminal end of exon 45 in the human dystrophin gene;
(b) a unit oligomer consisting of a nucleotide sequence complementary to a nucleotide sequence consisting of contiguous 7 to 16 bases selected from a nucleotide sequence located at positions 48 to 70 from the 5'-terminal end of exon 45 in the human dystrophin gene;
(c) a unit oligomer consisting of a nucleotide sequence complementary to a nucleotide sequence consisting of contiguous 7 to 16 bases selected from a nucleotide sequence located at positions 128 to 150 from the 5'-terminal end of exon 45 in the human dystrophin gene;
(d) a unit oligomer consisting of a nucleotide sequence complementary to a nucleotide sequence consisting of contiguous 7 to 16 bases selected from a nucleotide sequence located at positions 15 to 40 from the 5'-terminal end of exon 45 in the human dystrophin gene; and
(e) a unit oligomer consisting of a nucleotide sequence complementary to a nucleotide sequence consisting of contiguous 7 to 16 bases selected from a nucleotide sequence located at positions 110 to 125 from the 5'-terminal end of exon 45 in the human dystrophin gene.
[2] The antisense oligomer or pharmaceutically acceptable salt or hydrate thereof according to [1] above, wherein one of the two unit oligomers is (a).
[3] The antisense oligomer or pharmaceutically acceptable salt or hydrate thereof according to [1] or [2] above, which consists of any one nucleotide sequence selected from the group consisting of SEQ ID NOs: 7 to 12, 14 to 33, 40 to 52, 57, 64, 65 and 79 to 86.
[4] The antisense oligomer or pharmaceutically acceptable salt or hydrate thereof according to any one of [1] to [3] above, which consists of any one nucleotide sequence selected from the group consisting of SEQ ID NOs: 8, 10, 25, 30, 33, 79 and 80.
[5] The antisense oligomer or pharmaceutically acceptable salt or hydrate thereof according to any one of [1] to [4] above, which is an oligonucleotide.
[6] The antisense oligomer or pharmaceutically acceptable salt or hydrate thereof according to [5] above, wherein at least one nucleotide constituting the oligonucleotide is modified at the sugar moiety and/or at the phosphate bond moiety.
[7] The antisense oligomer or pharmaceutically acceptable salt or hydrate thereof according to [5] or [6] above, wherein the sugar moiety of at least one nucleotide constituting the oligonucleotide is a ribose in which the —OH group at the 2'-position is substituted with any group selected from the group consisting of OR, R, R'OR, SH, SR, $NH_2$, NHR, $NR_2$, $N_3$, CN, F, Cl, Br and I (wherein R represents alkyl or aryl, and R' represents alkylene).
[8] The antisense oligomer or pharmaceutically acceptable salt or hydrate thereof according to [6] or [7] above, wherein the phosphate bond moiety of at least one nucleotide constituting the oligonucleotide is any one selected from the group consisting of a phosphorothioate bond, a phosphorodithioate bond, an alkylphosphonate bond, a phosphoroamidate bond and a boranophosphate bond.
[9] The antisense oligomer according to any one of [1] to [4] above, which is a morpholino oligomer, or pharmaceutically acceptable salt or hydrate thereof.
[10] The antisense oligomer according to [9] above, which is a phosphorodiamidate morpholino oligomer, or pharmaceutically acceptable salt or hydrate thereof.
[11] The antisense oligomer according to [4] above, which is a phosphorodiamidate morpholino oligomer, or pharmaceutically acceptable salt or hydrate thereof.
[12] The antisense oligomer according to any one of [9] to [11] above, whose 5'-terminal end is any one of the groups represented by chemical formulae (1) to (3) shown below, or pharmaceutically acceptable salt or hydrate thereof.

[Formula 1]

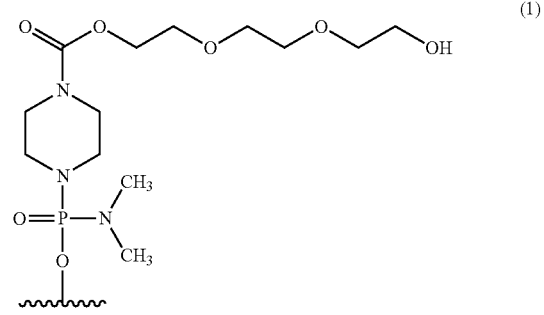

(1)

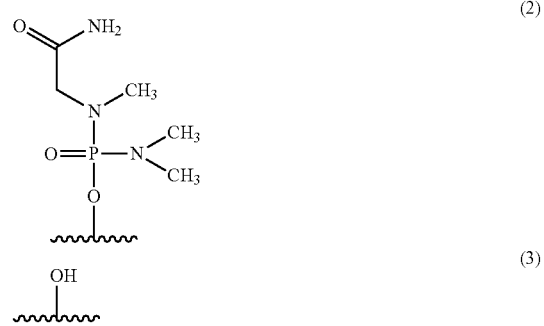

(2)

(3)

[13] A pharmaceutical composition for treatment of muscular dystrophy, which comprises the antisense oligomer or pharmaceutically acceptable salt or hydrate thereof according to any one of [1] to [12] above as an active ingredient.
[14] The pharmaceutical composition according to [13] above, which further comprises a pharmaceutically acceptable carrier.
[15] A method for treatment of muscular dystrophy, which comprises the step of administering a muscular dystrophy patient with the antisense oligomer or pharmaceutically acceptable salt or hydrate thereof according to any one of [1] to [12] above or with the pharmaceutical composition according to [13] or [14] above.
[16] The method for treatment according to [15] above, wherein the muscular dystrophy patient is a patient having a mutation to be targeted by exon 45 skipping in the dystrophin gene.
[17] The method for treatment according to [15] or [16] above, wherein the patient is a human patient.
[18] Use of the antisense oligomer or pharmaceutically acceptable salt or hydrate thereof according to any one of [1] to [12] above in the manufacture of a pharmaceutical composition for treatment of muscular dystrophy.
[19] The antisense oligomer or pharmaceutically acceptable salt or hydrate thereof according to any one of [1] to [12] above for use in the treatment of muscular dystrophy.
[20] The antisense oligomer or pharmaceutically acceptable salt or hydrate thereof according to [19] above, wherein in the treatment, a muscular dystrophy patient has a mutation to be targeted by exon 45 skipping in the dystrophin gene.
[21] The antisense oligomer or pharmaceutically acceptable salt or hydrate thereof according to [19] or [20] above, wherein the patient is a human patient.

Effects of the Invention

The antisense oligomer of the present invention allows effective induction of exon 45 skipping in the human dystrophin gene. In addition, the pharmaceutical composition of the present invention, when administered, allows effective alleviation of symptoms in Duchenne muscular dystrophy. Deleted exons in patients to be targeted include exons 18-44, 44, 46, 46-47, 46-48, 46-49, 46-51, 46-53, etc.

DESCRIPTION OF EMBODIMENTS

Figure 1:
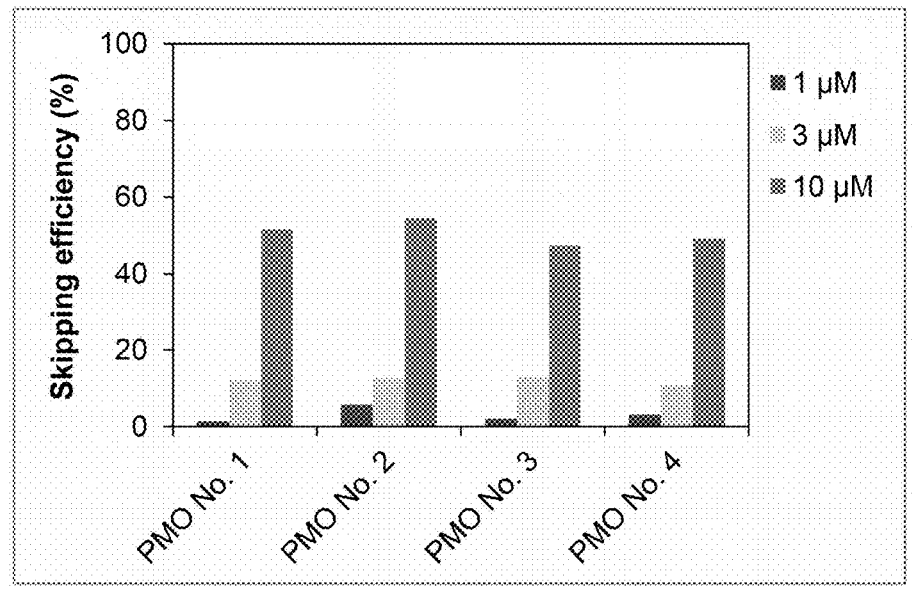
FIG. 1 is a graph showing the efficiency of exon 45 skipping in the human dystrophin gene in human rhabdomyosarcoma cells (RD cells).
Figure 2:
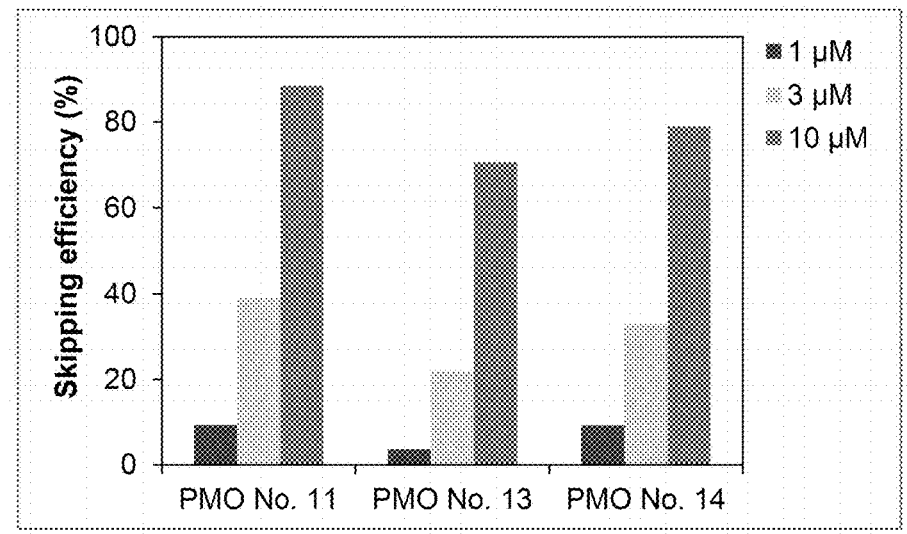
FIG. 2 is a graph showing the efficiency of exon 45 skipping in the human dystrophin gene in human rhabdomyosarcoma cells (RD cells).
Figure 3:
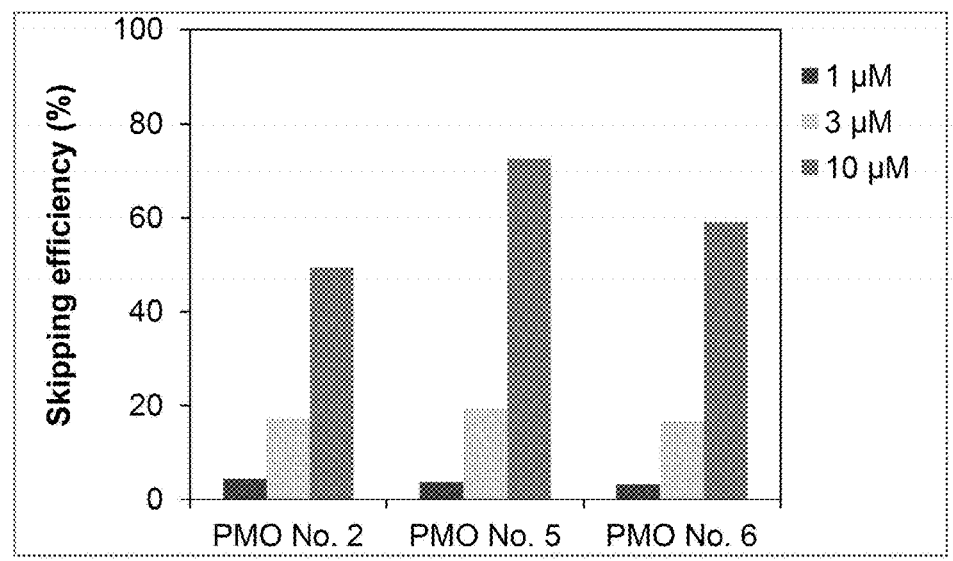
FIG. 3 is a graph showing the efficiency of exon 45 skipping in the human dystrophin gene in human rhabdomyosarcoma cells (RD cells).
Figure 4:
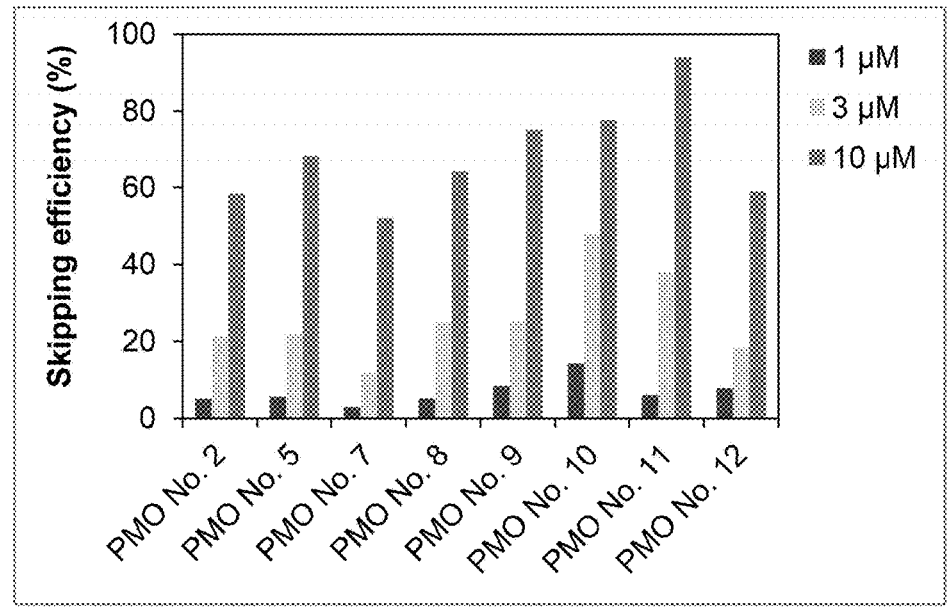
FIG. 4 is a graph showing the efficiency of exon 45 skipping in the human dystrophin gene in human rhabdomyosarcoma cells (RD cells).
Figure 5:
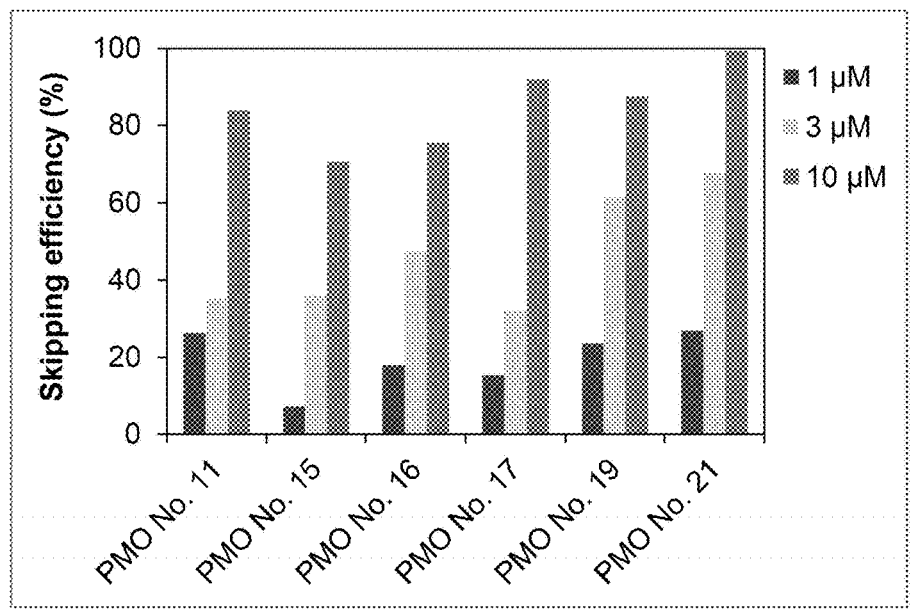
FIG. 5 is a graph showing the efficiency of exon 45 skipping in the human dystrophin gene in human rhabdomyosarcoma cells (RD cells).

The present invention will be described in more detail below. The following embodiments are illustrated to describe the present invention, and it is not intended to limit the present invention only to these embodiments. The present invention can be implemented in various modes without departing from the spirit of the present invention.
It should be noted that all publications cited herein, including prior art documents, patent gazettes and other patent documents, are incorporated herein by reference. Moreover, this specification incorporates the contents disclosed in the specification and drawings of Japanese Patent Application No. 2015-182145 (filed on Sep. 15, 2015), based on which the present application claims priority.

1. Antisense Oligomer

The present invention provides an antisense oligomer which allows exon 45 skipping in the human dystrophin gene, or a pharmaceutically acceptable salt or hydrate thereof (hereinafter collectively referred to as "the oligomer of the present invention").

[Exon 45 in the Human Dystrophin Gene]

In the context of the present invention, the term "gene" is intended to include not only a genomic gene, but also cDNA, precursor mRNA, and mRNA. The gene is preferably precursor mRNA, i.e., pre-mRNA.

In the human genome, the human dystrophin gene is located at locus Xp21.2. The human dystrophin gene has a size of 3.0 Mbp and is the largest gene among known human genes. However, the coding regions in the human dystrophin gene constitute only 14 kb and are distributed over 79 exons within the dystrophin gene (Roberts, R G., et al., Genomics, 16: 536-538 (1993)). Pre-mRNA transcribed from the human dystrophin gene is spliced to generate mature mRNA of 14 kb. The nucleotide sequence of the human wild-type dystrophin gene is known (GenBank Accession No. NM_004006).

The nucleotide sequence of exon 45 in the human wild-type dystrophin gene is shown in SEQ ID NO: 13. Moreover, in the nucleotide sequence (SEQ ID NO: 13) of exon 45 in the human wild-type dystrophin gene, a sequence consisting of bases at positions −5 to 15 counted from the 5'-terminal end is shown in SEQ ID NO: 3. Likewise, a sequence consisting of bases at positions 48 to 70, a sequence consisting of bases at positions 128 to 150, a sequence consisting of bases at positions 15 to 40 and a sequence consisting of bases at positions 110 to 125 are shown in SEQ ID NOs: 4 to 6 and 143, respectively.

The oligomer of the present invention has now been prepared to cause exon 45 skipping in the human dystrophin gene with the aim of modifying a protein encoded by the DMD dystrophin gene into a BMD dystrophin protein. Thus, exon 45 in the dystrophin gene to be skipped by the oligomer of the present invention includes not only wild-type, but also mutated forms.

More specifically, mutated exon 45 in the human dystrophin gene or a portion thereof is a polynucleotide shown in (I) or (II) below:
(I) a polynucleotide hybridizable under stringent conditions with a polynucleotide consisting of a nucleotide sequence complementary to any nucleotide sequence selected from the group consisting of SEQ ID NO: 13, SEQ ID NO: 3, SEQ ID NO: 4, SEQ ID NO: 5, SEQ ID NO: 6 and SEQ ID NO: 143; or
(II) a polynucleotide consisting of a nucleotide sequence sharing an identity of 90% or more with any nucleotide sequence selected from the group consisting of SEQ ID NO: 13, SEQ ID NO: 3, SEQ ID NO: 4, SEQ ID NO: 5, SEQ ID NO: 6 and SEQ ID NO: 143.

As used herein, the term "polynucleotide" is intended to mean DNA or RNA.

As used herein, the expression "polynucleotide hybridizable under stringent conditions" is intended to mean, for example, a polynucleotide that can be obtained by means of colony hybridization, plaque hybridization, Southern hybridization or other hybridization techniques using, as a probe, the whole or a part of a polynucleotide consisting of a nucleotide sequence complementary to any nucleotide sequence selected from the group consisting of SEQ ID NO: 13, SEQ ID NO: 3, SEQ ID NO: 4, SEQ ID NO: 5, SEQ ID NO: 6 and SEQ ID NO: 143. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the expression "nucleotide sequence complementary" is not limited only to a nucleotide sequence forming Watson-Crick pairs with a target nucleotide sequence and also includes nucleotide sequences forming wobble base pairs with a target nucleotide sequence. In this regard, a Watson-Crick pair is intended to mean a base pair which forms hydrogen bonding between adenine and thymine, between adenine and uracil or between guanine and cytosine, whereas a wobble base pair is intended to mean a base pair which forms hydrogen bonding between guanine and uracil, between inosine and uracil, between inosine and adenine or between inosine and cytosine. Moreover, such a "nucleotide sequence complementary" does not necessarily have 100% complementarity to a target nucleotide sequence and may contain non-complementary bases (e.g., 1 to 3 bases, 1 or 2 bases, or a single base) to the target nucleotide sequence.

As used herein, the term "stringent conditions" may be any of low stringent conditions, moderately stringent conditions and high stringent conditions. "Low stringent conditions" refer to, for example, conditions of 5×SSC, 5×Denhardt's solution, 0.5% SDS, 50% formamide at 32° C. Likewise, "moderately stringent conditions" refer to, for example, conditions of 5×SSC, 5×Denhardt's solution, 0.5% SDS, 50% formamide at 42° C. or conditions of 5×SSC, 1% SDS, 50 mM Tris-HCl (pH 7.5), 50% formamide at 42° C. "High stringent conditions" refer to, for example, conditions of 5×SSC, 5×Denhardt's solution, 0.5% SDS, 50% formamide at 50° C. or conditions of 0.2×SSC, 0.1% SDS at 65° C. Under these conditions, it can be expected that a polynucleotide having a higher identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol included in the kit, i.e., after a membrane is incubated overnight with a labeled probe and then washed with a primary washing buffer containing 0.1% (w/v) SDS at 55° C., the hybridized polynucleotide can be detected. Alternatively, if a commercially available reagent (e.g., PCR Labeling Mix (Roche Diagnostics)) is used for digoxigenin (DIG) labeling of a probe during probe preparation based on the whole or a part of a nucleotide sequence complementary to any nucleotide sequence selected from the group consisting of SEQ ID NO: 13, SEQ ID NO: 3, SEQ ID NO: 4, SEQ ID NO: 5, SEQ ID NO: 6 and SEQ ID NO: 143 or selected from the group consisting of SEQ ID NO: 3, SEQ ID NO: 4, SEQ ID NO: 5, SEQ ID NO: 6 and SEQ ID NO: 143, a DIG Nucleic Acid Detection Kit (Roche Diagnostics) may be used for detection of hybridization.

In addition to those listed above, other hybridizable polynucleotides include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with a sequence consisting of any polynucleotide selected from the group consisting of SEQ ID NO: 13, SEQ ID NO: 3, SEQ ID NO: 4, SEQ ID NO: 5, SEQ ID NO: 6 and SEQ ID NO: 143, as calculated by the homology search software BLAST using default parameters.

It should be noted that the identity of nucleotide sequences can be determined by using the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called BLASTN and BLASTX have been developed (Altschul S F, et al: J Mol Biol 215: 403, 1990). If BLASTN is used for nucleotide sequence analysis, parameters may be set to, for example, score=100 and wordlength=12. If BLAST and Gapped BLAST programs are used, default parameters in each program may be used.

In a certain embodiment, the oligomer of the present invention is an antisense oligomer of 14 to 32 bases in length comprising connected two unit oligomers selected from the group consisting of (a) to (e) shown below, or a pharmaceutically acceptable salt or hydrate thereof:
(a) a unit oligomer consisting of a nucleotide sequence complementary to a nucleotide sequence consisting of contiguous 7 to 16 bases selected from a nucleotide sequence located at positions −5 to 15 from the 5'-terminal end of exon 45 in the human dystrophin gene;
(b) a unit oligomer consisting of a nucleotide sequence complementary to a nucleotide sequence consisting of contiguous 7 to 16 bases selected from a nucleotide sequence located at positions 48 to 70 from the 5'-terminal end of exon 45 in the human dystrophin gene;
(c) a unit oligomer consisting of a nucleotide sequence complementary to a nucleotide sequence consisting of contiguous 7 to 16 bases selected from a nucleotide sequence located at positions 128 to 150 from the 5'-terminal end of exon 45 in the human dystrophin gene;
(d) a unit oligomer consisting of a nucleotide sequence complementary to a nucleotide sequence consisting of contiguous 7 to 16 bases selected from a nucleotide sequence located at positions 15 to 40 from the 5'-terminal end of exon 45 in the human dystrophin gene; and
(e) a unit oligomer consisting of a nucleotide sequence complementary to a nucleotide sequence consisting of contiguous 7 to 16 bases selected from a nucleotide sequence located at positions 110 to 125 from the 5'-terminal end of exon 45 in the human dystrophin gene.

The above unit oligomers (a) to (e) (hereinafter also simply referred to as "units") each have a size of 7 to 16 bases in length, preferably 8 to 16 bases in length, more preferably 9 to 16 bases in length. The respective units may be of the same or different size.

Moreover, when two unit oligomers are selected from the group consisting of (a) to (e), these two unit oligomers may be a combination of the same units (i.e., (a) and (a), (b) and (b), (c) and (c), (d) and (d), or (e) and (e)) or may be a combination of different units, but preferably a combination of different units. For example, if (a) is selected as one unit, the other unit is preferably any one of (b) to (e). Likewise, if (b) is selected as one unit, the other unit is preferably (a), (c), (d) or (e), while if (c) is selected as one unit, the other unit is preferably (a), (b), (d) or (e).

When two units are selected from (a) to (e), either of the selected two units may be located at the 5'-terminal side. If (a) and (b) are selected, the unit (a) is preferably connected to the 3'-terminal side. If (b) and (c) are selected, the unit (b) is preferably connected to the 3'-terminal side. If (a) and (c) are selected, the unit (a) is preferably connected to the 3'-terminal side. If (a) and (d) are selected, the unit (a) is preferably connected to the 3'-terminal side. If (a) and (e) are selected, the unit (a) is preferably connected to the 3'-terminal side.

As used here, the term "connected" is intended to mean that two units selected from (a) to (e) are directly connected to each other. Namely, when two units are connected, it means that the 3'-terminal end of the unit located at the 5'-terminal side and the 5'-terminal end of the unit located at the 3'-terminal side form a phosphate bond or any of the following groups:

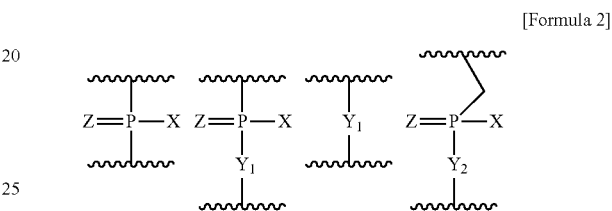

[Formula 2]

(wherein X represents —OH, —CH$_2$R$^1$, —O—CH$_2$R$^1$, —S—CH$_2$R$^1$, —NR$^2$R$^3$ or F;
R$^1$ represents H or alkyl;
R$^2$ and R$^3$, which may be the same or different, each represent H, alkyl, cycloalkyl or aryl;
Y$_1$ represents O, S, CH$_2$ or NR$^1$;
Y$_2$ represents 0, S or NR$^1$; and
Z represents O or S).

The expression "allowing exon 45 skipping in the human dystrophin gene" is intended to mean that upon binding the oligomer of the present invention to a site corresponding to exon 45 in a transcript (e.g., pre-mRNA) of the human dystrophin gene, the transcript is spliced to establish connection between a base corresponding to the 3'-terminal end of exon 43 and a base corresponding to the 5'-terminal end of exon 46 in the case of DMD patients with deletion of exon 44, by way of example, to thereby form mature mRNA free from codon frameshift.

The term "binding" is used here to mean that once the oligomer of the present invention has been mixed with a transcript of the human dystrophin gene, both will be hybridized with each other under physiological conditions to form a duplex. The expression "under physiological conditions" is used here to mean conditions adjusted to mimic in vivo pH, salt composition and temperature, as exemplified by conditions of 25° C. to 40° C., preferably 37° C., pH 5 to 8, preferably pH 7.4, and a sodium chloride concentration of 150 mM.

To confirm whether or not exon 45 skipping was caused in the human dystrophin gene, the oligomer of the present invention may be transfected into dystrophin-expressing cells (e.g., human rhabdomyosarcoma cells) and a region around exon 45 in mRNA of the human dystrophin gene may be amplified by RT-PCR from the total RNA of the above dystrophin-expressing cells, followed by nested PCR or sequencing analysis on the PCR amplification product. The efficiency of skipping may be determined as follows: mRNA of the human dystrophin gene is collected from test cells and the mRNA is measured for the polynucleotide level "A" in the band with exon 45 skipping and the polynucleotide level "B" in the band without exon 45 skipping, followed by calculation based on these measured values of "A" and "B" according to the following equation.

Skipping efficiency (%)=$A/(A+B) \times 100$

The oligomer of the present invention preferably causes exon 45 skipping with an efficiency of 10% or more, 20% or more, 30% or more, 40% or more, 50% or more, 60% or more, 70% or more, 80% or more, or 90% or more.

As to the calculation of skipping efficiency, reference may be made to WO2012/029986.

The oligomer of the present invention may be exemplified by an oligonucleotide, a morpholino oligomer or a peptide nucleic acid (PNA) oligomer, each being 14 to 32 bases in length. The oligomer of the present invention is preferably 16 to 30 bases, 17 to 30 bases, 18 to 30 bases, 19 to 30 bases, 20 to 30 bases, 20 to 29 bases, 20 to 28 bases, 20 to 27 bases, 20 to 26 bases or 21 to 26 bases in length, and is preferably a morpholino oligomer.

The above oligonucleotide (hereinafter referred to as "the oligonucleotide of the present invention") is an oligomer according to the present invention, whose constituent unit is a nucleotide, and such a nucleotide may be any of a ribonucleotide, a deoxyribonucleotide or a modified nucleotide.

A modified nucleotide refers to a ribonucleotide or deoxyribonucleotide whose nucleobase, sugar moiety and phosphate bond moiety are all or partly modified.

Examples of a nucleobase include adenine, guanine, hypoxanthine, cytosine, thymine, uracil, or modified bases thereof. Such modified bases may be exemplified by pseudouracil, 3-methyluracil, dihydrouracil, 5-alkylcytosines (e.g., 5-methylcytosine), 5-alkyluracils (e.g., 5-ethyluracil), 5-halouracils (e.g., 5-bromouracil), 6-azapyrimidine, 6-alkylpyrimidines (e.g., 6-methyluracil), 2-thiouracil, 4-thiouracil, 4-acetylcytosine, 5-(carboxyhydroxymethyl)uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine and so on, but are not limited thereto.

Modifications to the sugar moiety may be exemplified by modifications at the 2'-position of ribose and modifications at the other positions of sugar. Examples of modifications at the 2'-position of ribose include modifications intended to replace the —OH group at the 2'-position of ribose with OR, R, R'OR, SH, SR, $NH_2$, NHR, $NR_2$, $N_3$, CN, F, Cl, Br or I, wherein R represents alkyl or aryl, and R' represents alkylene.

Examples of modifications at the other positions of sugar include replacement of O with S at the 4'-position of ribose or deoxyribose, and bridging between 2'- and 4'-positions of sugar, as exemplified by LNAs (locked nucleic acids) or ENAs (2'-O,4'-C-ethylene-bridged nucleic acids), but are not limited thereto.

Modifications to the phosphate bond moiety may be exemplified by modifications intended to replace the phosphodiester bond with a phosphorothioate bond, a phosphorodithioate bond, an alkylphosphonate bond, a phosphoroamidate bond or a boranophosphate bond (Enya et al: Bioorganic & Medicinal Chemistry, 2008, 18, 9154-9160) (see, e.g., JP WO2006/129594 and JP WO2006/038608).

Alkyl is preferably a linear or branched alkyl containing 1 to 6 carbon atoms. More specifically, examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. Such an alkyl may be substituted with 1 to 3 substituents including halogen, alkoxy, cyano, nitro, etc.

Cycloalkyl is preferably a cycloalkyl containing 5 to 12 carbon atoms. More specifically, examples include cyclopentyl, cyclohexyl, cycloheptyl, cyclooctyl, cyclodecyl and cyclododecyl.

Halogens include fluorine, chlorine, bromine and iodine.

Alkoxy may be a linear or branched alkoxy containing 1 to 6 carbon atoms, as exemplified by methoxy, ethoxy, n-propoxy, isopropoxy, n-butoxy, isobutoxy, sec-butoxy, tert-butoxy, n-pentyloxy, isopentyloxy, n-hexyloxy, isohexyloxy and so on. Particularly preferred is an alkoxy containing 1 to 3 carbon atoms.

Aryl is preferably an aryl containing 6 to 10 carbon atoms. More specifically, examples include phenyl, α-naphthyl and β-naphthyl. Particularly preferred is phenyl. Such an aryl may be substituted with 1 to 3 substituents including alkyl, halogen, alkoxy, cyano, nitro, etc.

Alkylene is preferably a linear or branched alkylene containing 1 to 6 carbon atoms. More specifically, examples include methylene, ethylene, trimethylene, tetramethylene, pentamethylene, hexamethylene, 2-(ethyl)trimethylene and 1-(methyl)tetramethylene.

Acyl may be a linear or branched alkanoyl or an aroyl. Examples of such an alkanoyl include formyl, acetyl, 2-methylacetyl, 2,2-dimethylacetyl, propionyl, butyryl, isobutyryl, pentanoyl, 2,2-dimethylpropionyl, hexanoyl and so on. Examples of an aroyl include benzoyl, toluoyl and naphthoyl. Such an aroyl may be substituted at any substitutable position and may be substituted with alkyl(s).

The oligonucleotide of the present invention is preferably an oligomer according to the present invention, whose constituent unit is a group represented by the following general formula, in which the —OH group at the 2'-position of ribose is substituted with methoxy and the phosphate bond moiety is a phosphorothioate bond:

[Formula 3]

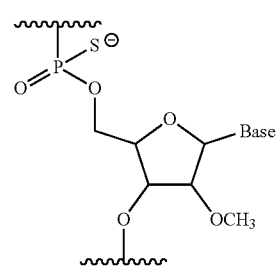

(wherein Base represents a nucleobase).

The oligonucleotide of the present invention may be readily synthesized with various automated synthesizers (e.g., AKTA oligopilot plus 10/100 (GE Healthcare)), or alternatively, its synthesis may be entrusted to a third party (e.g., Promega or Takara), etc.

The above morpholino oligomer is an oligomer according to the present invention, whose constituent unit is a group represented by the following general formula:

[Formula 4]

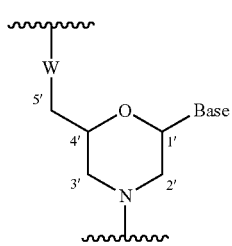

(wherein Base is the same as defined above; and

W represents a group shown by any of the following formulae:

[Formula 5]

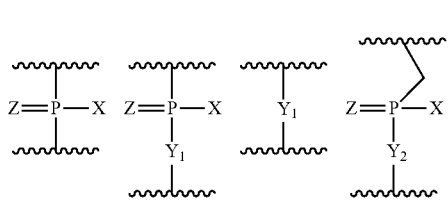

(wherein X represents —CH$_2$R$^1$, —O—CH$_2$R$^1$, —S—CH$_2$R$^1$, —NR$^2$R$^3$ or F;

R$^1$ represents H or alkyl;

R$^2$ and R$^3$, which may be the same or different, each represent H, alkyl, cycloalkyl or aryl;

Y$_1$ represents O, S, CH$_2$ or NR$^1$;

Y$_2$ represents O, S or NR$^1$; and

Z represents O or S)).

The morpholino oligomer is preferably an oligomer whose constituent unit is a group represented by the following formula (i.e., a phosphorodiamidate morpholino oligomer (hereinafter referred to as "PMO")):

[Formula 6]

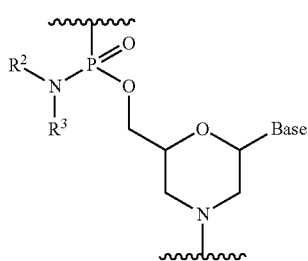

(wherein Base, R$^2$ and R$^3$ are the same as defined above).

For example, the morpholino oligomer may be prepared in accordance with WO1991/009033 or WO2009/064471. In particular, PMO may be prepared in accordance with the procedures described in WO2009/064471 or may be prepared in accordance with the procedures described in WO2013/100190.

[Process for PMO Preparation]

As one embodiment of PMO, a compound represented by the following general formula (I) (hereinafter referred to as PMO (I)) may be given by way of example:

[Formula 7]

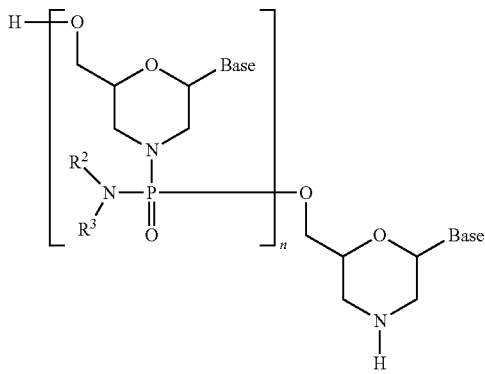

[wherein each Base, R$^2$ and R$^3$ are the same as defined above; and n is any integer in the range of 1 to 99, preferably any integer in the range of 13 to 31].

PMO (I) may be prepared in accordance with known procedures, for example, by conducting the operations shown in the following steps.

Compounds and reagents used in the following steps are not limited in any way as long as they are commonly used for PMO preparation.

Moreover, all the following steps may be accomplished by the liquid phase method or the solid phase method (repeating batch reactions or using a commercially available solid phase automated synthesizer). When PMO is prepared by the solid phase method, it is desirable to use an automated synthesizer in terms of simple operation and accurate synthesis.

(1) Step A:

This is a step where a compound represented by the following general formula (II) (hereinafter referred to as compound (II)) is treated with an acid to prepare a compound represented by the following general formula (III) (hereinafter referred to as compound (III)):

[Formula 8]

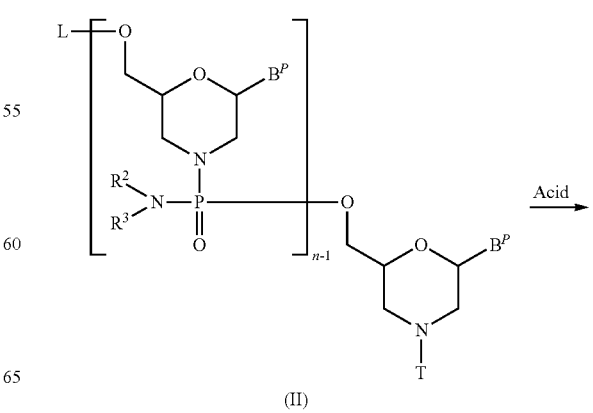

-continued

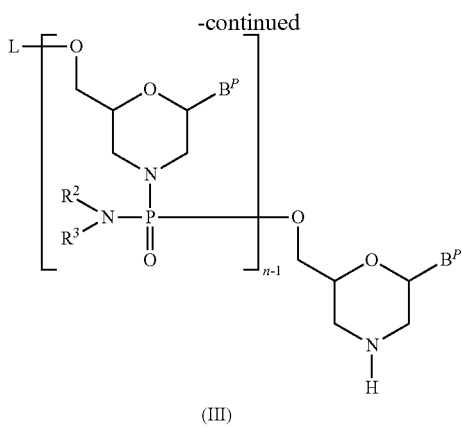

(III)

[wherein n, $R^2$ and $R^3$ are the same as defined above;

each $B^P$ independently represents a nucleobase which may be protected;

T represents a trityl group, a monomethoxytrityl group or a dimethoxytrityl group; and L represents hydrogen, acyl or a group represented by the following general formula (IV) (hereinafter referred to as group (IV))]:

[Formula 9]

(IV)

"Nucleobases" possible for $B^P$ may be exemplified by the same "nucleobases" as listed for Base, provided that amino groups or hydroxyl groups in these nucleobases for $B^P$ may be protected.

Protecting groups for these amino groups are not limited in any way as long as they are used as protecting groups for nucleic acids. More specifically, examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene. Protecting groups for hydroxyl groups include, for example, 2-cyanoethyl, 4-nitrophenethyl, phenylsulfonylethyl, methylsulfonylethyl, trimethylsilylethyl, phenyl which may be substituted with 1 to 5 electron withdrawing groups at any substitutable position(s), diphenylcarbamoyl, dimethylcarbamoyl, diethylcarbamoyl, methylphenylcarbamoyl, 1-pyrrolidinylcarbamoyl, morpholinocarbamoyl, 4-(tert-butylcarboxy)benzyl, 4-[(dimethylamino)carboxy]benzyl, and 4-(phenylcarboxy)benzyl (see, e.g., WO2009/064471).

The "solid carrier" is not limited in any way as long as it is a carrier available for use in the solid phase reaction of nucleic acids, but it is desirable to use, for example, a carrier which (i) is sparingly soluble in reagents available for use in the synthesis of morpholino nucleic acid derivatives (e.g., dichloromethane, acetonitrile, tetrazole, N-methylimidazole, pyridine, acetic anhydride, lutidine, trifluoroacetic acid), (ii) is chemically stable against the reagents available for use in the synthesis of morpholino nucleic acid derivatives, (iii) can be chemically modified, (iv) can be loaded with desired morpholino nucleic acid derivatives, (v) has strength sufficient to withstand high pressure during processing, and (vi) has a certain range of particle size and distribution. More specifically, examples include swellable polystyrene (e.g., aminomethyl polystyrene resin cross-linked with 1% divinylbenzene (200 to 400 mesh) (2.4 to 3.0 mmol/g) (Tokyo Chemical Industry Co., Ltd., Japan), Aminomethylated Polystyrene Resin HCl [divinylbenzene 1%, 100 to 200 mesh] (Peptide Institute, Inc., Japan)), non-swellable polystyrene (e.g., Primer Support (GE Healthcare)), PEG chain-attached polystyrenes (e.g., $NH_2$-PEG resin (Watanabe Chemical Industries, Ltd., Japan), TentaGel resin), controlled pore glass (CPG) (e.g., CPG Inc.), oxalylated controlled pore glass (see, e.g., Alul et al., Nucleic Acids Research, Vol. 19, 1527 (1991)), TentaGel support-aminopolyethylene glycol-derivatized support (see, e.g., Wright et al., Tetrahedron Letters, Vol. 34, 3373 (1993)), and a Poros-polystyrene/divinylbenzene copolymer.

As a "linker," it is possible to use a known linker which is commonly used to link a nucleic acid or a morpholino nucleic acid derivative, and examples include 3-aminopropyl, succinyl, 2,2'-diethanol sulfonyl, and a long-chain alkylamino (LCAA).

This step may be accomplished by treating compound (II) with an acid.

Examples of an "acid" available for use in this step include trifluoroacetic acid, dichloroacetic acid or trichloroacetic acid. The amount of an acid to be used is, for example, reasonably in the range of 0.1 molar equivalents to 1000 molar equivalents, preferably in the range of 1 molar equivalent to 100 molar equivalents, relative to 1 mole of compound (II).

Moreover, it is possible to use an organic amine together with the above acid. Any organic amine may be used for this purpose, and examples include triethylamine. The amount of an organic amine to be used is, for example, reasonably in the range of 0.01 molar equivalents to 10 molar equivalents, preferably in the range of 0.1 molar equivalents to 2 molar equivalents, relative to 1 mole of the acid.

In a case where an acid and an organic amine are used as a salt or mixture in this step, examples include a salt or mixture of trifluoroacetic acid and triethylamine, more specifically a mixture containing 2 equivalents of trifluoroacetic acid and 1 equivalent of triethylamine.

An acid available for use in this step may be used by being diluted with an appropriate solvent to give a concentration in the range of 0.1% to 30%. Any solvent may be used for this purpose as long as it is inert to the reaction, and examples include dichloromethane, acetonitrile, alcohols (e.g., ethanol, isopropanol, trifluoroethanol), water, or mixtures thereof.

The reaction temperature in the above reaction is, for example, preferably in the range of 10° C. to 50° C., more preferably in the range of 20° C. to 40° C., and even more preferably in the range of 25° C. to 35° C.

The reaction time will vary depending on the type of acid to be used and/or the reaction temperature, but it is generally reasonably in the range of 0.1 minutes to 24 hours, and preferably in the range of 1 minute to 5 hours.

Moreover, after completion of this step, a base may optionally be added to neutralize the acid remaining in the system. Any "base" may be used for this purpose and examples include diisopropylethylamine. Such a base may be used by being diluted with an appropriate solvent to give a concentration in the range of 0.1% (v/v) to 30% (v/v).

Any solvent may be used in this step as long as it is inert to the reaction, and examples include dichloromethane, acetonitrile, alcohols (e.g., ethanol, isopropanol, trifluoroethanol), water, or mixtures thereof. The reaction temperature is, for example, preferably in the range of 10° C. to 50° C., more preferably in the range of 20° C. to 40° C., and even more preferably in the range of 25° C. to 35° C.

The reaction time will vary depending on the type of base to be used and/or the reaction temperature, but it is generally reasonably in the range of 0.1 minutes to 24 hours, and preferably in the range of 1 minute to 5 hours.

It should be noted that compound (II) in which n=1 and L is group (IV), i.e., a compound represented by the following general formula (IIa) (hereinafter referred to as compound (IIa)) may be prepared in accordance with the following procedures:

[Formula 10]

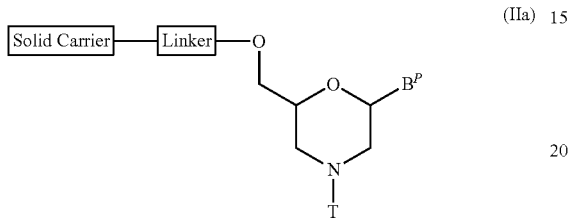

(IIa)

[wherein $B^P$, T, Linker and Solid carrier are the same as defined above].

Step 1:

This is a step where a compound represented by the following general formula (V) is treated with an acylating agent to prepare a compound represented by the following general formula (VI) (hereinafter referred to as compound (VI)):

[Formula 11]

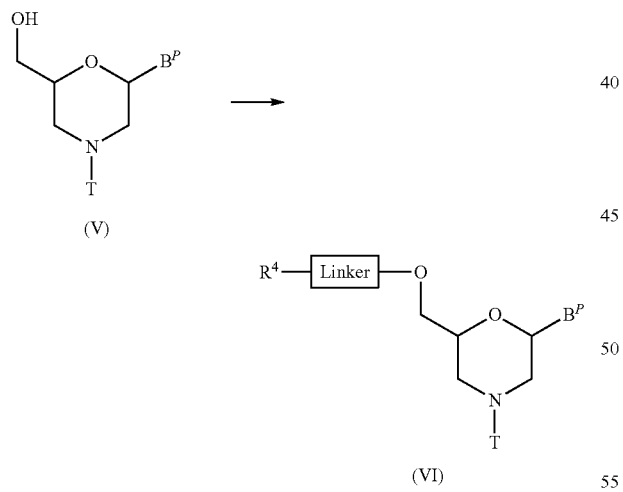

[wherein $B^P$, T and Linker are the same as defined above; and $R^4$ represents a hydroxyl group, halogen or amino].

This step may be accomplished starting from compound (V) by any known reaction for linker introduction.

In particular, a compound represented by the following general formula (VIa) may be prepared by any process known as esterification reaction with the use of compound (V) and succinic anhydride:

[Formula 12]

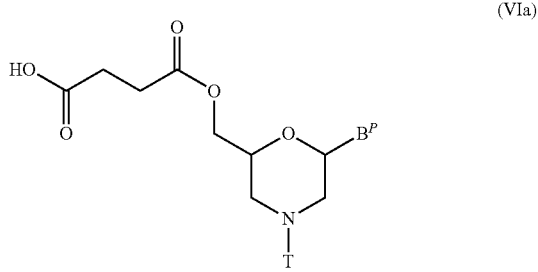

(VIa)

[wherein $B^P$ and T are the same as defined above].

Step 2:

This is a step where compound (VI) is reacted with a solid carrier by being treated with a condensing agent or the like to prepare compound (IIa):

[Formula 13]

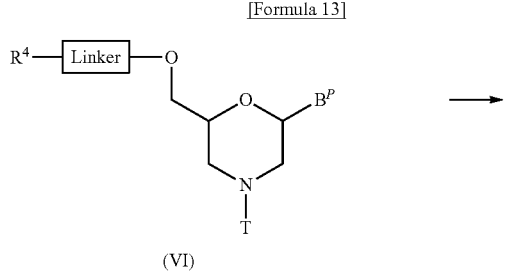

(VI)

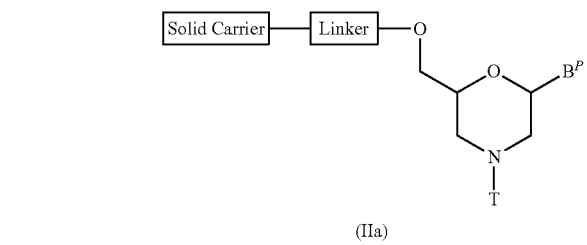

(IIa)

[wherein $B^P$, $R^4$, T, Linker and Solid carrier are the same as defined above].

This step may be accomplished by any process known as condensation reaction with the use of compound (VI) and a solid carrier.

Compound (II) in which n=2 to 99 and L is group (IV), i.e., a compound represented by the following general formula (IIa2) may be prepared starting from compound (IIa) by repeating desired times Steps A and B of the process for PMO preparation disclosed herein:

[Formula 14]

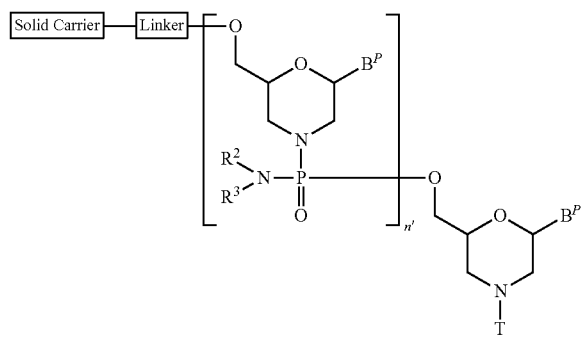

(IIa2)

[wherein $B^P$, $R^2$, $R^3$, T, Linker and Solid carrier are the same as defined above; and n' represents 1 to 98].

Likewise, compound (II) in which n=1 and L is hydrogen, i.e., a compound represented by the following general formula (IIb) may be prepared, for example, by the procedures described in WO1991/009033:

[Formula 15]

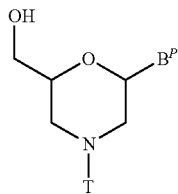

(IIb)

[wherein $B^P$ and T are the same as defined above].

Compound (II) in which n=2 to 99 and L is hydrogen, i.e., a compound represented by the following general formula (IIb2) may be prepared starting from compound (IIb) by repeating desired times Steps A and B of the process for PMO preparation disclosed herein:

[Formula 16]

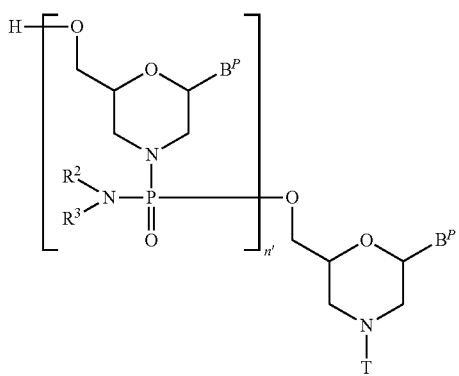

(IIb2)

[wherein $B^P$, n', $R^2$, $R^3$ and T are the same as defined above].

Likewise, compound (II) in which n=1 and L is acyl, i.e., a compound represented by the following general formula (IIc) may be prepared from compound (IIb) by any process known as acylation reaction:

[Formula 17]

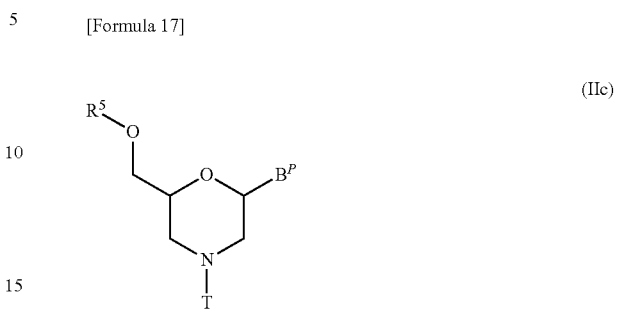

(IIc)

[wherein $B^P$ and T are the same as defined above; and $R^5$ represents acyl].

Compound (II) in which n=2 to 99 and L is acyl, i.e., a compound represented by the following general formula (IIc2) may be prepared starting from compound (IIc) by repeating desired times Steps A and B of the process for PMO preparation disclosed herein:

[Formula 18]

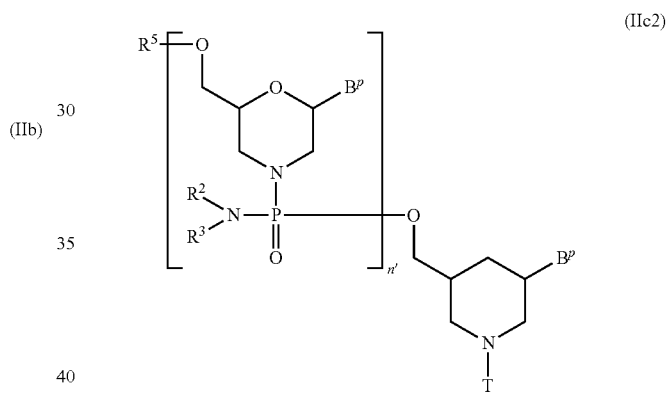

(IIc2)

[wherein $B^P$, n', $R^2$, $R^3$, $R^5$ and T are the same as defined above].

(2) Step B:

This is a step where compound (III) is treated with a morpholino monomer compound in the presence of a base to prepare a compound represented by the following general formula (VII) (hereinafter referred to as compound (VII)):

[Formula 19]

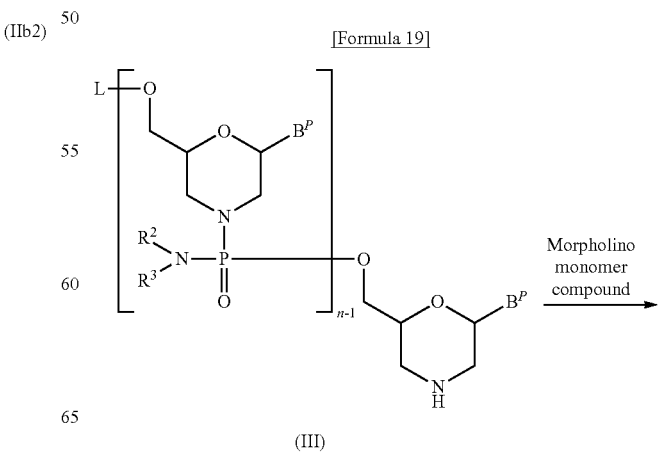

(III)

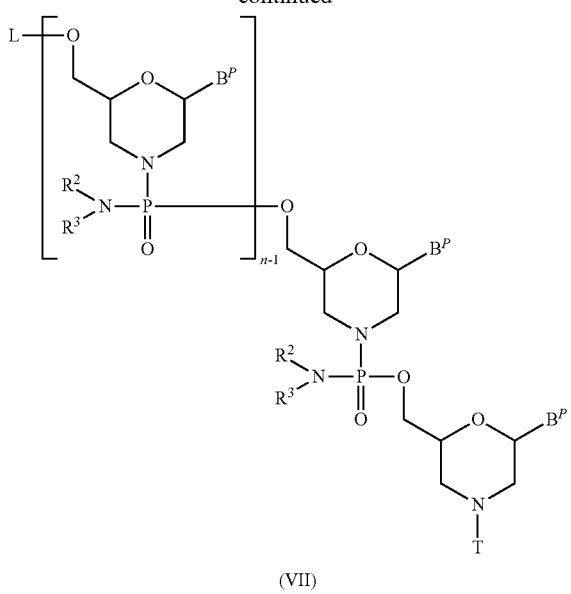

(VII)

[wherein each $B^P$, L, n, $R^2$, $R^3$ and T are the same as defined above].

This step may be accomplished by treating compound (III) with a morpholino monomer compound in the presence of a base.

Such a morpholino monomer compound may be exemplified by a compound represented by the following general formula (VIII):

[Formula 20]

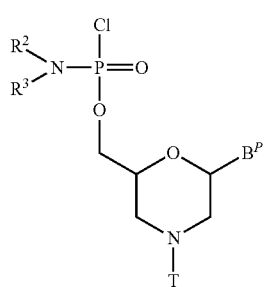

(VIII)

[wherein $B^P$, $R^2$, $R^3$ and T are the same as defined above].

Examples of a "base" available for use in this step include diisopropylethylamine, triethylamine or N-ethylmorpholine. The amount of a base to be used is, for example, reasonably in the range of 1 molar equivalent to 1000 molar equivalents, preferably in the range of 10 molar equivalents to 100 molar equivalents, relative to 1 mole of compound (III).

Such a morpholino monomer compound and a base available for use in this step may be used by being diluted with an appropriate solvent to give a concentration of 0.1% to 30%. Any solvent may be used for this purpose as long as it is inert to the reaction, and examples include N,N-dimethylimidazolidinone, N-methylpiperidone, DMF, dichloromethane, acetonitrile, tetrahydrofuran, or mixtures thereof.

The reaction temperature is, for example, preferably in the range of 0° C. to 100° C., and more preferably in the range of 10° C. to 50° C.

The reaction time will vary depending on the type of base to be used and/or the reaction temperature, but it is generally reasonably in the range of 1 minute to 48 hours, and preferably in the range of 30 minutes to 24 hours.

Moreover, after completion of this step, an acylating agent may optionally be added. Examples of an "acylating agent" include acetic anhydride, acetyl chloride and phenoxyacetic anhydride. Such an acylating agent may be used by being diluted with an appropriate solvent to give a concentration in the range of 0.1% to 30%, by way of example. Any solvent may be used for this purpose as long as it is inert to the reaction, and examples include dichloromethane, acetonitrile, alcohols (e.g., ethanol, isopropanol, trifluoroethanol), water, or mixtures thereof.

If necessary, it is possible to use a base (e.g., pyridine, lutidine, collidine, triethylamine, diisopropylethylamine, N-ethylmorpholine) together with an acylating agent. The amount of an acylating agent to be used is preferably in the range of 0.1 molar equivalents to 10000 molar equivalents, and more preferably in the range of 1 molar equivalent to 1000 molar equivalents. The amount of a base to be used is, for example, reasonably in the range of 0.1 molar equivalents to 100 molar equivalents, preferably in the range of 1 molar equivalent to 10 molar equivalents, relative to 1 mole of an acylating agent.

The reaction temperature in this reaction is preferably in the range of 10° C. to 50° C., more preferably in the range of 10° C. to 50° C., even more preferably in the range of 20° C. to 40° C., and still even more preferably in the range of 25° C. to 35° C. The reaction time will vary, e.g., depending on the type of acylating agent to be used and/or the reaction temperature, but it is generally reasonably in the range of 0.1 minutes to 24 hours, and preferably in the range of 1 minute to 5 hours.

(3) Step C:

This is a step where a deprotecting agent is used to remove the protecting groups from compound (VII) prepared in Step B, thereby preparing a compound represented by general formula (IX):

[Formula 21]

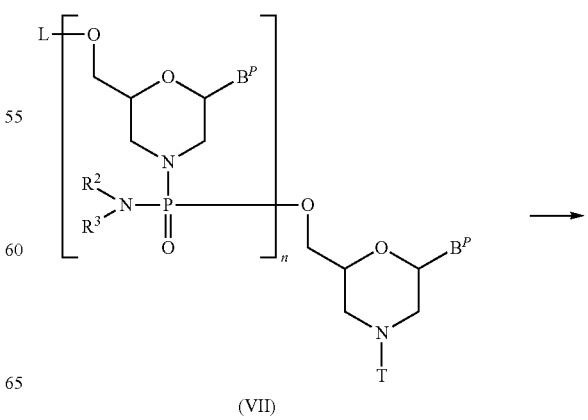

(VII)

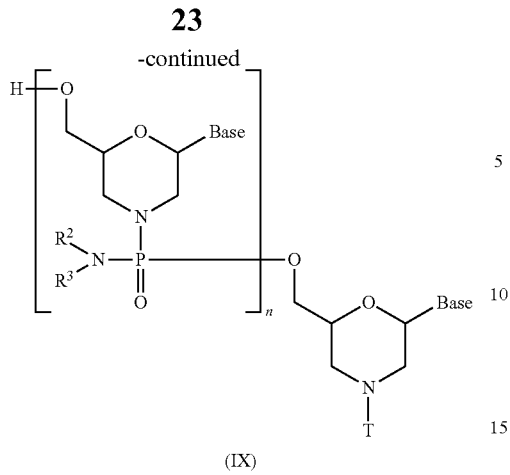

(IX)

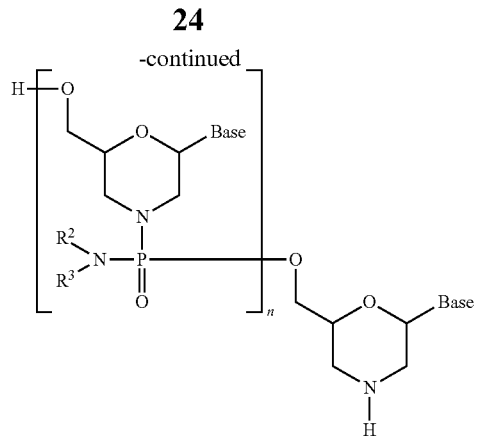

(I)

[wherein Base, $B^P$, L, n, $R^2$, $R^3$ and T are the same as defined above].

This step may be accomplished by treating compound (VII) with a deprotecting agent.

Examples of a "deprotecting agent" include concentrated aqueous ammonia and methylamine. Such a "deprotecting agent" available for use in this step may be used by being diluted with water, methanol, ethanol, isopropyl alcohol, acetonitrile, tetrahydrofuran, DMF, N,N-dimethylimidazolidinone, N-methylpiperidone, or a mixed solvent thereof. Among them, preferred is ethanol. The amount of a deprotecting agent to be used is, for example, reasonably in the range of 1 molar equivalent to 100000 molar equivalents, preferably in the range of 10 molar equivalents to 1000 molar equivalents, relative to 1 mole of compound (VII), by way of example.

The reaction temperature is, for example, reasonably in the range of 15° C. to 75° C., preferably in the range of 40° C. to 70° C., and more preferably in the range of 50° C. to 60° C. The reaction time for deprotection will vary depending on the type of compound (VII) and/or the reaction temperature, etc., but it is reasonably in the range of 10 minutes to 30 hours, preferably in the range of 30 minutes to 24 hours, and more preferably in the range of 5 hours to 20 hours.

(4) Step D:

This is a step where compound (IX) prepared in Step C is treated with an acid to prepare PMO (I):

[Formula 22]

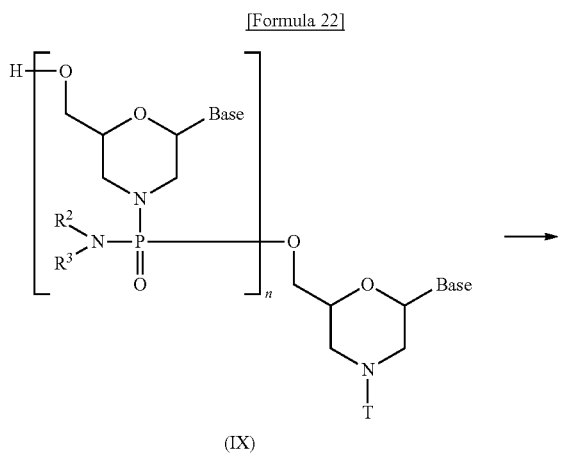

(IX)

→

[wherein Base, n, $R^2$, $R^3$ and T are the same as defined above].

This step may be accomplished by adding an acid to compound (IX).

Examples of an "acid" available for use in this step include trichloroacetic acid, dichloroacetic acid, acetic acid, phosphoric acid and hydrochloric acid, etc. As to the amount of an acid to be used, it is reasonable to use the acid in an amount to give a solution pH, for example, in the range of 0.1 to 4.0, more preferably in the range of 1.0 to 3.0. Any solvent may be used in this step as long as it is inert to the reaction, and examples include acetonitrile, water, or mixed solvents thereof.

The reaction temperature is preferably in the range of 10° C. to 50° C., more preferably in the range of 20° C. to 40° C., and even more preferably in the range of 25° C. to 35° C. The reaction time for deprotection will vary depending on the type of compound (IX) and/or the reaction temperature, etc., but it is reasonably in the range of 0.1 minutes to 5 hours, preferably in the range of 1 minute to 1 hour, and more preferably in the range of 1 minute to 30 minutes.

PMO (I) may be obtained from the reaction mixture obtained in this step by commonly used separation and purification means including extraction, concentration, neutralization, filtration, centrifugation, recrystallization, $C_8$ to $C_{18}$ reversed-phase column chromatography, cation exchange column chromatography, anion exchange column chromatography, gel filtration column chromatography, high performance liquid chromatography, dialysis, ultrafiltration and other means, which may be used either alone or in combination, whereby desired PMO (I) can be isolated and purified (see, e.g., WO1991/09033).

In the case of using reversed-phase chromatography for purification of PMO (I), a mixed solution of 20 mM triethylamine/acetate buffer and acetonitrile may be used as an elution solvent, by way of example.

Likewise, in the case of using ion exchange chromatography for purification of PMO (I), a mixed solution of 1 M aqueous sodium chloride and 10 mM aqueous sodium hydroxide may be used, by way of example.

The above peptide nucleic acid oligomer is an oligomer according to the present invention, whose constituent unit is a group represented by the following general formula:

[Formula 23]

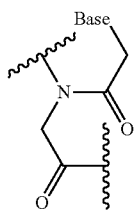

(wherein Base is the same as defined above).

Peptide nucleic acids may be prepared, for example, in accordance with the documents listed below.
1) P. E. Nielsen, M. Egholm, R. H. Berg, O. Buchardt, Science, 254, 1497 (1991)
2) M. Egholm, O. Buchardt, P. E. Nielsen, R. H. Berg, Jacs., 114, 1895 (1992)
3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G. Batz, K. Otteson, H. Orum, J. Pept. Res., 49, 80 (1997)

Moreover, the oligomer of the present invention may be configured such that its 5'-terminal end is any one of the groups represented by chemical formulae (1) to (3) shown below, with (3) —OH being preferred.

[Formula 24]

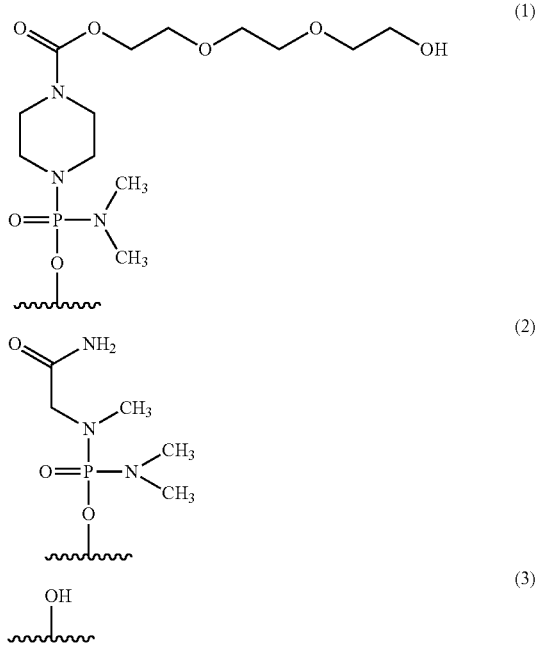

The groups represented by the above formulae (1), (2) and (3) are hereinafter referred to as "group (1)," "group (2)" and "group (3)," respectively.

2. Pharmaceutical Composition

The oligomer of the present invention allows exon 45 skipping in the dystrophin gene. It is therefore expected that the symptoms of muscular dystrophy can be alleviated when a pharmaceutical composition comprising the oligomer of the present invention is administered to DMD patients having a mutation targeted by exon 45 skipping (i.e., a mutation is converted to in-flame by exon 45 skipping) in their dystrophin gene. Moreover, because of its short chain length, the oligomer of the present invention is advantageous in that its preparation steps are simple and further in that its preparation costs can be reduced.

Thus, in another embodiment, the present invention provides a pharmaceutical composition for treatment of muscular dystrophy, which comprises the oligomer of the present invention, a pharmaceutically acceptable salt or hydrate thereof as an active ingredient (hereinafter referred to as "the composition of the present invention").

Examples of a pharmaceutically acceptable salt of the oligomer of the present invention contained in the composition of the present invention include alkali metal salts (e.g., sodium salt, potassium salt, lithium salt); alkaline earth metal salts (e.g., calcium salt, magnesium salt); metal salts (e.g., aluminum salt, iron salt, zinc salt, copper salt, nickel salt, cobalt salt); ammonium salt; organic amine salts (e.g., t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt); halogenated hydroacid salts (e.g., hydrofluoride salt, hydrochloride salt, hydrobromide salt, hydroiodide salt); inorganic acid salts (i.e., nitrate salt, perchlorate salt, sulfate salt, phosphate salt); lower alkanesulfonic acid salts (e.g., methanesulfonate salt, trifluoromethanesulfonate salt, ethanesulfonate salt); arylsulfonic acid salts (e.g., benzenesulfonate salt, p-toluenesulfonate salt); organic acid salts (e.g., acetate salt, malate salt, fumarate salt, succinate salt, citrate salt, tartrate salt, oxalate salt, maleate salt); amino acid salts (e.g., glycine salt, lysine salt, arginine salt, ornithine salt, glutamate salt, aspartate salt), etc. These salts may be prepared in any known manner. Alternatively, the oligomer of the present invention contained in the composition of the present invention may be in the form of a hydrate thereof.

The composition of the present invention may be administered in any pharmaceutically acceptable mode, which may be selected as appropriate for the intended therapeutic method. However, in terms of easy delivery to muscle tissue, preferred are intravenous administration, intraarterial administration, intramuscular administration, subcutaneous administration, oral administration, interstitial administration, percutaneous administration and so on. Moreover, the composition of the present invention may be in any dosage form, and examples include various types of injections, oral formulations, drops, inhalants, ointments, lotions, etc.

In a case where the oligomer of the present invention is administered to muscular dystrophy patients, the composition of the present invention preferably comprises a carrier which promotes the delivery of the oligomer to muscle tissue. Such a carrier is not limited in any way as long as it is pharmaceutically acceptable, and examples include cationic carriers (e.g., cationic liposomes, cationic polymers) or viral envelope-based carriers. Examples of cationic liposomes include liposomes formed from 2-O-(2-diethylaminoethyl)carbamoyl-1,3-O-dioleoyl glycerol and a phospholipid as essential constituent members (hereinafter referred to as "liposome A"), Oligofectamine® (Invitrogen), Lipofectin® (Invitrogen), Lipofectamine® (Invitrogen), Lipofectamine 2000® (Invitrogen), DMRIE-C® (Invitrogen), GeneSilencer® (Gene Therapy Systems), TransMessenger® (QIAGEN), TransIT TKO® (Mirus) and Nucleofector II (Lonza). Among them, preferred is liposome A. Examples of cationic polymers include JetSI® (Qbiogene) and Jet-PEI® (polyethyleneimine, Qbiogene). Examples of viral envelope-based carriers include GenomeOne® (HVJ-E liposomes, Ishihara Sangyo Kaisha, Ltd., Japan). Alternatively, it is also possible to use the pharmaceutical device shown in Japanese Patent No. 2924179 or the cationic carriers shown in JP WO2006/129594 and JP WO2008/096690.

The concentration of the oligomer of the present invention contained in the composition of the present invention will vary, e.g., depending on the type of carrier, but it is reasonably in the range of 0.1 nM to 100 μM, preferably in the range of 1 nM to 10 μM, and more preferably in the range of 10 nM to 1 μM. Likewise, the weight ratio of the carrier to the oligomer of the present invention contained in the composition of the present invention (i.e., the carrier/oligomer ratio) will vary, e.g., depending on the properties of the oligomer and the type of the carrier, but it is reasonably in the range of 0.1 to 100, preferably in the range of 1 to 50, and more preferably in the range of 10 to 20.

The composition of the present invention may optionally comprise a pharmaceutically acceptable additive, in addition to the oligomer of the present invention and the carrier described above. Examples of such an additive include an emulsifier aid (e.g., a fatty acid containing 6 to 22 carbon atoms or a pharmaceutically acceptable salt thereof, albumin, dextran), a stabilizing agent (e.g., cholesterol, phosphatidic acid), an isotonizing agent (e.g., sodium chloride, glucose, maltose, lactose, sucrose, trehalose), and a pH adjuster (e.g., hydrochloric acid, sulfuric acid, phosphoric acid, acetic acid, sodium hydroxide, potassium hydroxide, triethanolamine). These additives may be used either alone or in combination. The content of the additive(s) in the composition of the present invention is reasonably 90% by weight or less, preferably 70% by weight or less, and more preferably 50% by weight or less.

The composition of the present invention may be prepared by adding the oligomer of the present invention to a dispersion of a carrier, followed by adequate stirring. An additive (s) may be added at any appropriate stage, either before or after adding the oligomer of the present invention. Any aqueous solvent may be used for adding the oligomer of the present invention as long as it is pharmaceutically acceptable, and examples include injectable water, injectable distilled water, electrolytic solutions (e.g., physiological saline), and sugar solutions (e.g., glucose solution, maltose solution). Moreover, in this case, conditions including pH and temperature may be selected as appropriate by those skilled in the art.

The composition of the present invention may be formulated into a solution or a lyophilized formulation thereof, by way of example. Such a lyophilized formulation may be prepared in a standard manner by freeze-drying the composition of the present invention in a solution form. For example, the composition of the present invention in a solution form may be sterilized as appropriate and then dispensed in given amounts into vial bottles, followed by preliminary freezing under conditions of about −40° C. to −20° C. for about 2 hours, primary drying at about 0° C. to 10° C. under reduced pressure and then secondary drying at about 15° C. to 25° C. under reduced pressure. Moreover, in most cases, the vials may be purged with a nitrogen gas and then capped, thereby giving a lyophilized formulation of the composition of the present invention.

Such a lyophilized formulation of the composition of the present invention may generally be used after being reconstituted by addition of any appropriate solution (i.e., a reconstituting solution). Examples of such a reconstituting solution include injectable water, physiological saline, and other commonly used infusion solutions. The volume of such a reconstituting solution will vary, e.g., depending on the intended use and is not limited in any way, but it is reasonably 0.5- to 2-fold greater than the solution volume before freeze-drying, or 500 mL or less.

The dose for administration of the composition of the present invention is desirably adjusted in consideration of the type of the oligomer of the present invention contained therein, the intended dosage form, the condition of a patient such as age and body weight, the route of administration, and the nature and severity of a disease. However, the daily dose for adults is generally in the range of 0.1 mg to 10 g/human, preferably in the range of 1 mg to 1 g/human, calculated as the amount of the oligomer of the present invention. This numerical range may vary depending on the type of disease to be targeted, the mode of administration, and/or the type of target molecule. Thus, a dose lower than this range may be sufficient in some cases, or conversely, a dose higher than this range should be required in some cases. Moreover, the composition of the present invention may be administered once to several times a day or at intervals of one to several days.

In another embodiment, the composition of the present invention may be a pharmaceutical composition comprising a vector capable of expressing the oligonucleotide of the present invention and a carrier as described above. Such an expression vector may be capable of expressing a plurality of oligonucleotides according to the present invention. Such a composition may optionally comprise a pharmaceutically acceptable additive, as in the case of the composition of the present invention comprising the oligomer of the present invention. The concentration of the expression vector contained in this composition will vary, e.g., depending on the type of carrier, but it is reasonably in the range of 0.1 nM to 100 μM, preferably in the range of 1 nM to 10 μM, and more preferably in the range of 10 nM to 1 μM. The weight ratio of the carrier to the expression vector contained in this composition (i.e., the carrier/expression vector ratio) will vary, e.g., depending on the properties of the expression vector and the type of the carrier, but it is reasonably in the range of 0.1 to 100, preferably in the range of 1 to 50, and more preferably in the range of 10 to 20. Moreover, the content of the carrier contained in this composition is the same as in the case of the composition of the present invention comprising the oligomer of the present invention, and procedures for preparation are also the same as in the case of the composition of the present invention.

The present invention will be further described in more detail below by way of the following illustrative examples and test examples, although the present invention is not limited thereto.

EXAMPLES

Reference Example 1

4-{[(2S,6R)-6-(4-Benzamido-2-oxopyrimidin-1-yl)-4-tritylmorpholin-2-yl]methoxy}-4-oxobutanoic acid loaded on aminopolystyrene resin Step 1: Preparation of 4-{[(2S,6R)-6-(4-benzamido-2-oxopyrimidin-1(2H)-yl)-4-tritylmorpholin-2-yl]methoxy}-4-oxobutanoic acid Under an argon atmosphere, N-{1-[(2R,6S)-6-(hydroxymethyl)-4-tritylmorpholin-2-yl]-2-oxo-1,2-dihydropyrimidin-4-yl}benzamide (3.44 g) and 4-dimethylaminopyridine (4-DMAP) (1.1 g) were suspended in dichloromethane (50 mL), and succinic anhydride (0.90 g) was then added thereto, followed by stirring at room temperature for 3 hours. The reaction solution was mixed with methanol (10 mL) and concentrated under reduced pressure. The residue was extracted with ethyl acetate and 0.5 M aqueous potassium dihydrogen phosphate. The resulting organic layer was washed sequentially with 0.5 M aqueous potassium dihydrogen phosphate, water and saturated aqueous sodium chloride. The resulting organic layer was dried over sodium sulfate and concentrated under reduced pressure to obtain 4.0 g of the desired product.

Step 2: Preparation of 4-{[(2S,6R)-6-(4-benzamido-2-oxopyrimidin-1-yl)-4-tritylmorpholin-2-yl]methoxy}-4-oxobutanoic acid loaded on aminopolystyrene resin 4-{[(2S,6R)-6-(4-Benzamido-2-oxopyrimidin-1 (2H)-yl)-4-tritylmorpholin-2-yl]methoxy}-4-oxobutanoic acid (4.0 g) was dissolved in pyridine (dehydrated) (200 mL), followed by addition of 4-DMAP (0.73 g) and 1-ethyl-3-(3-dimethylaminopropyl)-carbodiimide hydrochloride (11.5 g). Then, aminopolystyrene resin Primer support 200 amino (GE Healthcare Japan, 17-5214-97) (25.0 g) and triethylamine (8.5 mL) were added to this mixture, followed by shaking at room temperature for 4 days. After the reaction, the resin was collected by filtration. The resulting resin was washed sequentially with pyridine, methanol and dichloromethane, and then dried under reduced pressure. To the resulting resin, tetrahydrofuran (dehydrated) (200 mL), acetic anhydride (15 mL) and 2,6-lutidine (15 mL) were added, followed by shaking at room temperature for 2 hours. The resin was collected by filtration, washed sequentially with pyridine, methanol and dichloromethane, and then dried under reduced pressure to obtain 26.7 g of the desired product.

To determine the loading amount of the desired product, the molar amount of trityl per gram of the resin was measured in a known manner as UV absorbance at 409 nm. The loading amount on the resin was found to be 129.2 µmol/g.

Conditions for UV measurement
Instrument: U-2910 (Hitachi, Ltd., Japan)
Solvent: methanesulfonic acid
Wavelength: 409 nm
ε value: 45000

Reference Example 2

4-{[(2 S,6R)-6-(5-Methyl-2,4-dioxopyrimidin-1-yl)-4-tritylmorpholin-2-yl]methoxy}-4-oxobutanoic acid loaded on aminopolystyrene resin The same procedures as shown in Reference Example 1 were repeated to prepare the titled compound, except that N-{1-[(2R,6S)-6-(hydroxymethyl)-4-tritylmorpholin-2-yl]-2-oxo-1,2-dihydropyrimidin-4-yl}benzamide used in Step 1 of Reference Example 1 was replaced in this step with 1-[(2R,6S)-6-(hydroxymethyl)-4-tritylmorpholin-2-yl]-5-methylpyrimidine-2,4(1H,3H)-dione.

To determine the loading amount of the desired product, the molar amount of trityl per gram of the resin was measured in a known manner as UV absorbance at 409 nm. The loading amount on the resin was found to be 164.0 µmol/g.

Reference Example 3

4-{[(2S,6R)-6-(6-Benzamidopurin-9-yl)-4-tritylmorpholin-2-yl]methoxy}-4-oxobutanoic acid loaded on aminopolystyrene resin The same procedures as shown in Reference Example 1 were repeated to prepare the titled compound, except that N-{1-[(2R,6S)-6-(hydroxymethyl)-4-tritylmorpholin-2-yl]-2-oxo-1,2-dihydropyrimidin-4-yl}benzamide used in Step 1 of Reference Example 1 was replaced in this step with N-{9-[(2R,6S)-6-(hydroxymethyl)-4-tritylmorpholin-2-yl]purin-6-yl}benzamide.

To determine the loading amount of the desired product, the molar amount of trityl per gram of the resin was measured in a known manner as UV absorbance at 409 nm. The loading amount on the resin was found to be 185.7 µmol/g.

Reference Example 4

4-{{(2S,6R)-6-{6-(2-Cyanoethoxy)-2-[(2-phenoxyacetyl)amino]purin-9-yl}-4-tritylmorpholin-2-yl}methoxy}-4-oxobutanoic acid loaded on aminopolystyrene resin The same procedures as shown in Reference Example 1 were repeated to prepare the titled compound, except that N-{1-[(2R,6S)-6-(hydroxymethyl)-4-tritylmorpholin-2-yl]-2-oxo-1,2-dihydropyrimidin-4-yl}benzamide used in Step 1 of Reference Example 1 was replaced in this step with N-{6-(2-cyanoethoxy)-9-[(2R,6S)-6-(hydroxymethyl)-4-tritylmorpholin-2-yl]purin-2-yl}-2-phenoxyacetamide.

To determine the loading amount of the desired product, the molar amount of trityl per gram of the resin was measured in a known manner as UV absorbance at 409 nm. The loading amount on the resin was found to be 164.8 µmol/g.

In accordance with the descriptions in Example 1 shown below, PMOs having the nucleotide sequences of PMO Nos. 1 to 81 indicated in Table 1 were synthesized (wherein $R^2$ and $R^3$ are each methyl, and the 5'-terminal end is group (3)). The thus synthesized PMOs were each dissolved in water for injection (Otsuka Pharmaceutical Factory, Inc., Japan).

| PMO No. | Nucleotide sequence | Sequence name | SEQ ID NO: |
|---|---|---|---|
| [TABLE 1-1] | | | |
| 1 | TTGCCGCTGCCCACATCCTGGAGTTC | H45_1-13_18-30 | 14 |
| 2 | GTTTGCCGCTGCCTCCTGGAGTTCCT | H45_-2-11_20-32 | 7 |
| 3 | GCCGCTGCCCACATCCTGGAGTTCCT | H45_-2-13_18-28 | 15 |
| 4 | CCGCTGCCCAATGTCCTGGAGTTCCT | H45_-2-11_15-27 | 16 |
| 5 | TTGCCGCTGCCCATCCTGGAGTTCCT | H45_-2-11_18-30 | 17 |
| 6 | TTTGCCGCTGCCATCCTGGAGTTCCT | H45_-2-13_21-31 | 18 |

-continued

| PMO No. | Nucleotide sequence | Sequence name | SEQ ID NO: |
|---|---|---|---|
| 7 | TTTGCCGCTGCCTCCTGGAGTTCC | H45_-1-11_20-31 | 19 |
| 8 | TGCCGCTGCCCGCCATCCTGGAGTTCC | H45_1-15_19-29 | 20 |
| 9 | GTTTGCCGCTGCCCTGGAGTTCCT | H45_-2-10_21-32 | 8 |
| 10 | CAGTTTGCCGCTGCCCATCCTGGAGTTCCT | H45_-2-13_20-34 | 9 |
| 11 | CAGTTTGCCGCTGCCCTGGAGTTCCT | H45_-2-8_19-34 | 10 |
| 12 | GTTTGCCGCTGCCATCCTGGAGTTC | H45_1-12_20-32 | 21 |
| 13 | CAGTTTGCCGCTGCTGGAGTTCCT | H45_-2-8_21-34 | 22 |
| 14 | ACAGTTTGCCGCTCTGGAGTTCCT | H45_-2-9_23-35 | 23 |
| 15 | CAGTTTGCCGCTGCCGGAGTTCCT | H45_-2-7_20-34 | 24 |
| 16 | GTTTGCCGCTGCCCTGGAGTTCC | H45_-1-8_19-32 | 25 |
| 17 | CAGTTTGCCGCTGCCGGAGTTCCTG | H45_-3-7_20-34 | 26 |
| 18 | CCGCTGCCCAATGTGGAGTTCCTGT | H45_-4-8_15-27 | 27 |
| 19 | CAGTTTGCCGCTGCCCTGGAGTTC | H45_1-8_19-34 | 28 |
| 20 | CCGCTGCCCAATCTGGAGTTCCT | H45_-2-9_16-27 | 29 |
| 21 | CAGTTTGCCGCTGCCCTGGAGTTCC | H45_-1-8_19-34 | 30 |
| 22 | TTGCCGCTGCCCACTGGAGTTCCT | H45_-2-9_18-30 | 31 |
| 23 | TTGCCGCTGCCCACTGGAGTTCCTGT | H45_-4-9_18-30 | 32 |
| 24 | ACAGTTTGCCGCCTGGAGTTCC | H45_-1-10_25-35 | 33 |
| 25 | GTTTGCCGCTGC | H45_21-32 | 34 |
| 26 | CCTGGAGTTCCT | H45_-2-10 | 35 |
| 27 | TGGAGTTCCT | H45_-2-8 | 36 |
| 28 | CAGTTTGCCGCTGCCC | H45_19-34 | 37 |
| 29 | TCTTCCCCAGTTGCCATCCTGGAGTT | H45_2-14_53-65 | 38 |
| 30 | AGACCTCCTGCCACCATCCTGGAGTT | H45_2-14_136-148 | 39 |
| 31 | TTCTTCCCCAGTTGCGCCATCCTGGAGTTC | H45_1-15_52-66 | 11 |
| 32 | CAGACCTCCTGCCACGCCATCCTGGAGTTC | H45_1-15_135-149 | 12 |
| 33 | GACCTCCTGCCACCATCCTGGAGTTC | H45_1-14_136-147 | 40 |

[TABLE 1-2]

| 34 | TCCCCAGTTGCGCCATCCTGGAGTTC | H45_1-15_52-62 | 41 |
|---|---|---|---|
| 35 | GACCTCCTGCCGCCATCCTGGAGTTC | H45_1-15_137-147 | 42 |
| 36 | CTTCCCCAGTTGCCATCCTGGAGTTC | H45_1-14_53-64 | 43 |
| 37 | TTCCCCAGTTGCACATCCTGGAGTTC | H45_1-13_51-63 | 44 |
| 38 | CCTCCTGCCACGCCATCCTGGAGTTC | H45_1-13_133-145 | 45 |
| 39 | ACCTCCTGCCACCCATCCTGGAGTTC | H45_1-13_134-146 | 46 |
| 40 | TTTCTTCCCCAGTCATCCTGGAGTTC | H45_1-13_55-67 | 47 |
| 41 | GCAGACCTCCTGCCATCCTGGAGTTC | H45_1-13_138-150 | 48 |
| 42 | TTCTTCCCCAGTTGCCATCCTGGAGTTC | H45_1-13_52-66 | 49 |
| 43 | CCCCAGTTGCATCTGGAGTTCCT | H45_-2-9_50-61 | 50 |
| 44 | TTCTTCCCCAGTTGCCCTGGAGTTCC | H45_-1-10_52-66 | 51 |
| 45 | CTTCCCCAGTTGCCATCCTGGAGTTCCT | H45_-2-13_52-64 | 52 |
| 46 | CAGACCTCCTGCCACTCCTGGAGTTC | H45_1-11_135-149 | 53 |
| 47 | TGCAGACCTCCTGCCTCTGGAGTTC | H45_1-11_137-151 | 54 |
| 48 | CTGTTTGCAGACCCATCCTGGAGTTC | H45_1-13_144-156 | 55 |
| 49 | TTTGCAGACCTCCTGGAGTTCCTGTA | H45_-5-8_141-153 | 56 |
| 50 | CCTGCCACCGCAGATGCCATCCTGGAGTTC | H45_1-15_128-142 | 57 |
| 51 | ACCTCCTGCCACCGCTTGCCGCTGCCCAAT | H45_16-30_132-146 | 58 |
| 52 | TCCTGTAGAATACCATCCTGGAGTTC | H45_1-13_98-110 | 59 |
| 53 | CTCCTGCCACCGCTGGCATCTGTTTT | H45_85-97_132-144 | 60 |
| 54 | ACCTCCTGCCACCGCTCTTCCCCAGTTGCA | H45_51-65_132-146 | 61 |
| 55 | TGGCATCTGTTTTCATCCTGGAGTTC | H45_1-13_85-97 | 62 |
| 56 | TTATTTCTTCCCCAGTTCCTGTAAGA | H45_-8-5_58-70 | 63 |
| 57 | GCTTCCCAATGCCATCCTGGAGTTCC | H45_-1-15_114-123 | 64 |
| 58 | GGCTTCCCAATGCCATCCTGGAGTTC | H45_1-15_114-124 | 65 |
| 59 | TTTCTGTCTGACAGCTCCTGCCACCGCAGA | H45_129-143_156-170 | 66 |
| 60 | TCCTGCCACCGCAGAGAGGATTGCTGAATT | H45_69-83_129-143 | 67 |
| 61 | TCCTGCCACCGCAGACTGGCATCTGTTTTT | H45_84-98_129-143 | 68 |
| 62 | TCCTGCCACCGCAGATTTTCCTGTAGAATA | H45_99-113_129-143 | 69 |
| 63 | GCCATCCTGGAGTTC | H45_1-15 | 70 |
| 64 | TTCTTCCCCAGTTGC | H45_52-66 | 71 |
| 65 | CAGACCTCCTGCCAC | H45_135-149 | 72 |
| 66 | TCCTGGAGTTCCT | H45_-2-11 | 73 |
| 67 | GTTTGCCGCTGCC | H45_20-32 | 74 |
| 68 | CTCCTGCCACCGCGCCGCTGCCCAAT | H45_16-28_132-144 | 75 |

[TABLE 1-3]

| 69 | ATTCAGGCTTCCCTTCCCCAGTTGCA | H45_51-63_117-129 | 76 |
|---|---|---|---|
| 70 | TGGAGTTCC | H45_-1-8 | 77 |
| 71 | TGGAGTTC | H45_1-8 | 78 |
| 72 | CAGTTTGCCGCCTGGAGTTCC | H45_-1-10_25-34 | 79 |
| 73 | ACAGTTTGCCGCTGGAGTTCCT | H45_-2-9_25-35 | 80 |
| 74 | GTTTGCCGCTGCCTGGAGTTCC | H45_-1-8_20-32 | 81 |
| 75 | AACAGTTTGCCCCTGGAGTTCC | H45_-1-10_26-36 | 82 |
| 76 | CAGTTTGCCGCCTGGAGTTC | H45_1-10_25-34 | 83 |

-continued

| PMO No. | Nucleotide sequence | Sequence name | SEQ ID NO: |
|---|---|---|---|
| 77 | CAGTTTGCCGCTCCTGGAGTTC | H45_1-11_24-34 | 84 |
| 78 | AGTTTGCCGCTCCTGGAGTTC | H45_1-11_24-33 | 85 |
| 79 | ACAGTTTGCCGCTGGAGTTCC | H45_-1-9_25-35 | 86 |
| 80 | TGCCGCTGCCCATCCTGGAGTTCC | H45_-1-11_18-29 | 87 |
| 81 | CTGCCACCGCAGCCGCTGCCCAATGC | H45_14-27_130-141 | 88 |
| 82 | CCTGGAGTTCC | H45_-1-10 | 144 |
| 83 | CAGTTTGCCG | H45_25-34 | 145 |
| 84 | ACAGTTTGCCG | H45_25-35 | 146 |

Example 1

4-{[(2S,6R)-6-(4-Benzamido-2-oxopyrimidin-1 (2H)-yl)-4-tritylmorpholin-2-yl]methoxy}-4-oxobutanoic acid loaded on aminopolystyrene resin (Reference Example 1) or 4-{[(2S,6R)-6-(5-methyl-2,4-dioxopyrimidin-1-yl)-4-tritylmorpholin-2-yl]methoxy}-4-oxobutanoic acid loaded on aminopolystyrene resin (Reference Example 2) or 4-{[(2 S,6R)-6-(6-benzamidopurin-9-yl)-4-tritylmorpholin-2-yl]methoxy}-4-oxobutanoic acid loaded on aminopolystyrene resin (Reference Example 3) or 4-{{(2S,6R)-6-{6-(2-cyanoethoxy)-2-[(2-phenoxyacetyl)amino]purin-9-yl}-4-tritylmorpholin-2-yl}methoxy}-4-oxobutanoic acid loaded on aminopolystyrene resin (Reference Example 4), each corresponding to the 5'-terminal base, was filled in an amount of 0.2 g into a column equipped with a filter to initiate the following synthesis cycles using a nucleic acid synthesizer (AKTA Oligopilot 10 plus). To give the nucleotide sequence of each compound indicated in Table 1, a desired morpholino monomer compound was added in each coupling cycle (see Table 2 below).

TABLE 2

| Step | Reagent | Volume (mL) | Time (min) |
|---|---|---|---|
| 1 | Deblocking solution | 18 to 32 | 1.8 to 3.2 |
| 2 | Neutralizing/washing solution | 30 | 1.5 |
| 3 | Coupling solution B | 5 | 0.5 |
| 4 | Coupling solution A | 1.3 | 0.25 |
| 5 | Coupling reaction with the reagents charged in Steps 3 and 4 | | 120 to 300 |
| 6 | Acetonitrile | 20 | 1.0 |
| 7 | Capping solution | 9 | 2.0 |
| 8 | Acetonitrile | 30 | 2.0 |

(Note) Only in the case of 3'-terminal acetylation, Steps 1, 2, 7 and 8 were repeated again after the final cycle.

It should be noted that the deblocking solution used was a dichloromethane solution containing 3% (w/v) trifluoroacetic acid. The neutralizing/washing solution used was prepared by dissolving N,N-diisopropylethylamine at 10% (v/v) and tetrahydrofuran at 5% (v/v) in a dichloromethane solution containing 35% (v/v) acetonitrile. The coupling solution A used was prepared by dissolving a morpholino monomer compound at 0.10 M in tetrahydrofuran. The coupling solution B used was prepared by dissolving N,N-diisopropylethylamine at 20% (v/v) and tetrahydrofuran at 10% (v/v) in acetonitrile. The capping solution used was prepared by dissolving acetic anhydride at 20% (v/v) and 2,6-lutidine at 30% (v/v) in acetonitrile. The aminopolystyrene resin loaded with PMO synthesized as above was collected from the reaction vessel and dried at room temperature for 2 hours or longer under reduced pressure. The dried PMO loaded on the aminopolystyrene resin was charged into a reaction vessel and 5 mL of 28% aqueous ammonia-ethanol (1/4) was added thereto, followed by stirring at 55° C. for 15 hours. The aminopolystyrene resin was separated by filtration and washed with 1 mL of water-ethanol (1/4). The resulting filtrate was concentrated under reduced pressure. The resulting residue was dissolved in 10 mL of a mixed solvent containing 20 mM acetic acid-triethylamine buffer (TEAA buffer) and acetonitrile (4/1), and then filtered through a membrane filter. The resulting filtrate was purified by reversed-phase HPLC. The conditions used are as indicated in Table 3 below.

TABLE 3

| Column | XBridge 5 µm C18 (Waters, φ19 × 50 mm, 1 CV = 14 mL) |
|---|---|
| Flow rate | 10 mL/minute |
| Column temperature | room temperature |
| Solution A | 20 mM TEAA buffer |
| Solution B | CH$_3$CN |
| Gradient | (B) conc. 10% → 70%/15 CV |

CV: column volume

The fractions were each analyzed to collect the desired product, which was then concentrated under reduced pressure. The concentrated residue was diluted with 2 M aqueous phosphoric acid (0.5 mL) and stirred for 15 minutes. Further, the residue was made alkaline with 2 M aqueous sodium hydroxide (2 mL) and filtered through a membrane filter (0.45 µm).

The resulting aqueous solution containing the desired product was purified through an anion exchange resin column. The conditions used are as indicated in Table 4 below.

TABLE 4

| Column | Source 15 Q (GE Healthcare, φ10 × 108 mm, 1 CV = 8.5 mL) |
|---|---|
| Flow rate | 8.5 mL/min |
| Column temperature | room temperature |
| Solution A | 10 mM aqueous sodium hydroxide |
| Solution B | 10 mM aqueous sodium hydroxide, 1M aqueous sodium chloride |
| Gradient | (B) conc. 1% → 50%/40 CV |

The fractions were each analyzed (by HPLC) to obtain the desired product as an aqueous solution. The resulting aqueous solution was neutralized with 0.1 M phosphate buffer (pH 6.0) and then desalted by reversed-phase HPLC under the conditions indicated in Table 5 below.

TABLE 5

| Column | XBridge 5 μm C8 (Waters, φ10 × 50 mm, 1 CV = 4 mL) |
|---|---|
| Flow rate | 4 mL/minute |
| Column temperature | 60° C. |
| Solution A | water |

TABLE 5-continued

| Solution B | CH$_3$CN |
|---|---|
| Gradient | (B) conc. 0% → 50%/20 CV |

The desired product was collected and concentrated under reduced pressure. The resulting residue was dissolved in water and freeze-dried to obtain the desired compound as a white flocculent solid. The calculated and measured values of ESI-TOF-MS are shown in Table 6.

| PMO No. | Nucleotide sequence | Calculated value | Measured value |
|---|---|---|---|
| [TABLE 6-1] | | | |
| 1 | TTGCCGCTGCCCACATCCTGGAGTTC | 8520.95 | 8520.65 |
| 2 | GTTTGCCGCTGCCTCCTGGAGTTCCT | 8542.94 | 8542.57 |
| 3 | GCCGCTGCCCACATCCTGGAGTTCCT | 8505.95 | 8506.57 |
| 4 | CCGCTGCCCAATGTCCTGGAGTTCCT | 8520.95 | 8521.37 |
| 5 | TTGCCGCTGCCCATCCTGGAGTTCCT | 8511.94 | 8511.70 |
| 6 | TTTGCCGCTGCCATCCTGGAGTTCCT | 8526.94 | 8527.07 |
| 7 | TTTGCCGCTGCCTCCTGGAGTTCC | 7857.71 | 7857.32 |
| 8 | TGCCGCTGCCCGCCATCCTGGAGTTC | 8521.95 | 8521.98 |
| 9 | GTTTGCCGCTGCCCTGGAGTTCCT | 7897.72 | 7897.71 |
| 10 | CAGTTTGCCGCTGCCCATCCTGGAGTTCCT | 9851.40 | 9851.60 |
| 11 | CAGTTTGCCGCTGCCCTGGAGTTCCT | 8551.95 | 8551.80 |
| 12 | GTTTGCCGCTGCCATCCTGGAGTTC | 8236.84 | 8236.69 |
| 13 | CAGTTTGCCGCTGCTGGAGTTCCT | 7921.73 | 7921.91 |
| 14 | ACAGTTTGCCGCTCTGGAGTTCCT | 7905.73 | 7905.53 |
| 15 | CAGTTTGCCGCTGCCGGAGTTCCT | 7906.73 | 7906.65 |
| 16 | GTTTGCCGCTGCCCTGGAGTTCC | 7567.61 | 7567.35 |
| 17 | CAGTTTGCCGCTGCCGGAGTTCCTG | 8261.85 | 8261.67 |
| 18 | CCGCTGCCCAATGTGGAGTTCCTGT | 8245.85 | 8245.68 |
| 19 | CAGTTTGCCGCTGCCCTGGAGTTC | 7906.73 | 7906.70 |
| 20 | CCGCTGCCCAATCTGGAGTTCCT | 7520.61 | 7520.60 |
| 21 | CAGTTTGCCGCTGCCCTGGAGTTCC | 8221.84 | 8221.48 |
| 22 | TTGCCGCTGCCCACTGGAGTTCCT | 7866.72 | 7866.77 |
| 23 | TTGCCGCTGCCCACTGGAGTTCCTGT | 8551.95 | 8552.23 |
| 24 | ACAGTTTGCCGCCTGGAGTTCC | 7245.51 | 7245.48 |
| 25 | GTTTGCCGCTGC | 3912.36 | 3912.16 |
| 26 | CCTGGAGTTCCT | 3896.36 | 3896.12 |
| 27 | TGGAGTTCCT | 3266.14 | 3265.99 |
| 28 | CAGTTTGCCGCTGCCC | 5196.81 | 5196.30 |
| 29 | TCTTCCCCAGTTGCCATCCTGGAGTT | 8510.93 | 8511.8 |
| 30 | AGACCTCCTGCCACCATCCTGGAGTT | 8513.95 | 8513.72 |
| 31 | TTCTTCCCCAGTTGCGCCATCCTGGAGTTC | 9826.39 | 9826.15 |
| 32 | CAGACCTCCTGCCACGCCATCCTGGAGTTC | 9814.41 | 9813.82 |
| 33 | GACCTCCTGCCACCATCCTGGAGTTC | 8489.95 | 8490.01 |
| [TABLE 6-2] | | | |
| 34 | TCCCCAGTTGCGCCATCCTGGAGTTC | 8520.95 | 8520.97 |
| 35 | GACCTCCTGCCGCCATCCTGGAGTTC | 8505.95 | 8506.48 |
| 36 | CTTCCCCAGTTGCCATCCTGGAGTTC | 8495.94 | 8495.43 |
| 37 | TTCCCCAGTTGCACATCCTGGAGTTC | 8519.95 | 8520.35 |
| 38 | CCTCCTGCCACCGCATCCTGGAGTTC | 8465.94 | 8466.23 |
| 39 | ACCTCCTGCCACCCATCCTGGAGTTC | 8449.94 | 8449.88 |
| 40 | TTTCTTCCCCAGTCATCCTGGAGTTC | 8485.93 | 8486.01 |
| 41 | GCAGACCTCCTGCCATCCTGGAGTTC | 8529.96 | 8529.54 |
| 42 | TTCTTCCCCAGTTGCCATCCTGGAGTTC | 9156.16 | 9156.62 |
| 43 | CCCCAGTTGCATCTGGAGTTCCT | 7535.61 | 7535.92 |
| 44 | TTCTTCCCCAGTTGCCCTGGAGTTCC | 8486.93 | 8486.27 |
| 45 | CTTCCCCAGTTGCCATCCTGGAGTTCCT | 9141.16 | 9141.18 |
| 46 | CAGACCTCCTGCCACTCCTGGAGTTC | 8489.95 | 8489.65 |
| 47 | TGCAGACCTCCTGCCTCCTGGAGTTC | 8520.95 | 8520.58 |
| 48 | CTGTTTGCAGACCCATCCTGGAGTTC | 8559.96 | 8560.66 |
| 49 | TTTGCAGACCTCCTGGAGTTCCTGTA | 8574.96 | 8574.85 |
| 50 | CCTGCCACCGCAGATGCCATCCTGGAGTTC | 9854.42 | 9854.07 |
| 51 | ACCTCCTGCCACCGCTTGCCGCTGCCCAAT | 9750.39 | 9750.67 |
| 52 | TCCTGTAGAATACCATCCTGGAGTTC | 8567.97 | 8567.11 |
| 53 | CTCCTGCCACCGCTGGCATCTGTTTT | 8486.93 | 8486.39 |
| 54 | ACCTCCTGCCACCGCTCTTCCCCAGTTGCA | 9725.38 | 9725.57 |
| 55 | TGGCATCTGTTTTCATCCTGGAGTTC | 8580.95 | 8580.81 |
| 56 | TTATTTCTTCCCCAGTTCCTGTAAGA | 8508.94 | 8508.7 |
| 57 | GCTTCCCAATGCCATCCTGGAGTTCC | 8504.95 | 8504.88 |
| 58 | GGCTTCCCAATGCCATCCTGGAGTTC | 8544.96 | 8544.72 |
| 59 | TTTCTGTCTGACAGCTCCTGCCACCGCAGA | 9844.41 | 9844.1 |
| 60 | TCCTGCCACCGCAGAGAGGATTGCTGAATT | 9957.45 | 9957.8 |

| PMO No. | Nucleotide sequence | Calculated value | Measured value |
|---|---|---|---|
| 61 | TCCTGCCACCGCAGACTGGCATCTGTTTTT | 9850.4 | 9850.45 |
| 62 | TCCTGCCACCGCAGATTTTCCTGTAGAATA | 9867.42 | 9867.85 |
| 63 | GCCATCCTGGAGTTC | 4905.71 | 4905.02 |
| 64 | TTCTTCCCCAGTTGC | 4831.68 | 4831.14 |
| 65 | CAGACCTCCTGCCAC | 4819.7 | 4819.64 |
| 66 | TCCTGGAGTTCCT | 4226.47 | 4226.03 |
| 67 | GTTTGCCGCTGCC | 4227.47 | 4227.48 |
| 68 | CTCCTGCCACCGCGCCGCTGCCCAAT | 8435.93 | 8436.58 |

[TABLE 6-3]

| | | | |
|---|---|---|---|
| 69 | ATTCAGGCTTCCCTTCCCCAGTTGCA | 8479.93 | 8479.03 |
| 70 | TGGAGTTCC | 2936.03 | 2936.07 |
| 71 | TGGAGTTC | 2620.92 | 2620.97 |
| 72 | CAGTTTGCCGCCTGGAGTTCC | 6906.39 | 6906.44 |
| 73 | ACAGTTTGCCGCTGGAGTTCCT | 7260.51 | 7260.67 |
| 74 | GTTTGCCGCTGCCTGGAGTTCC | 7252.5 | 7252.48 |
| 75 | AACAGTTTGCCCCTGGAGTTCC | 7229.51 | 7229.07 |
| 76 | CAGTTTGCCGCCTGGAGTTC | 6591.28 | 6591.07 |
| 77 | CAGTTTGCCGCTCCTGGAGTTC | 7236.5 | 7236.76 |
| 78 | AGTTTGCCGCTCCTGGAGTTC | 6921.39 | 6921.06 |
| 79 | ACAGTTTGCCGCTGGAGTTCC | 6930.4 | 6930.42 |
| 80 | TGCCGCTGCCCATCCTGGAGTTCC | 7851.72 | 7852.1 |
| 81 | CTGCCACCGCAGCCGCTGCCCAATGC | 8484.96 | 8484.68 |
| 82 | CCTGGAGTTCC | 3566.25 | 3566.51 |
| 83 | CAGTTTGCCG | 3251.14 | 3251.19 |
| 84 | ACAGTTTGCCG | 3590.26 | 3590.04 |

Test Example 1

In Vitro Assay

Into $3.5 \times 10^5$ RD cells (human rhabdomyosarcoma cell line), the antisense oligomers shown in Table 1 were each transfected at 1 to 10 μM through Nucleofector II (Lonza) using an Amaxa Cell Line Nucleofector Kit L. The program used was T-030.

After transfection, the cells were cultured for three nights at 37° C. under 5% $CO_2$ conditions in 2 mL of Eagle's minimal essential medium (EMEM) (SIGMA; the same applies hereinafter) containing 10% fetal bovine serum (FBS) (Invitrogen).

After the cells were washed once with PBS (Nissui Pharmaceutical Co., Ltd., Japan; the same applies hereinafter), 350 μL of Buffer RLT (QIAGEN) containing 1% 2-mercaptoethanol (Nacalai Tesque, Inc., Japan) was added to the cells, and the cells were lysed by being allowed to stand at room temperature for a few minutes. The cell lysate was collected into a QIAshredder homogenizer (QIAGEN) and centrifuged at 15,000 rpm for 2 minutes to prepare a homogenate. The total RNA was extracted in accordance with the protocol attached to an RNeasy Mini Kit (QIAGEN). The concentration of the extracted total RNA was measured with a NanoDrop ND-1000 spectrophotometer (LMS Co., Ltd., Japan).

One-Step RT-PCR was performed on 400 ng of the extracted total RNA using a QIAGEN OneStep RT-PCR Kit (QIAGEN). A reaction solution was prepared in accordance with the protocol attached to the kit. The thermal cycler used was PTC-100 (MJ Research) or TaKaRa PCR Thermal Cycler Dice Touch (Takara Bio Inc., Japan). The RT-PCR program used is as shown below.

50° C. for 30 minutes: reverse transcription reaction

95° C. for 15 minutes: polymerase activation, reverse transcriptase inactivation, cDNA thermal denaturation

[94° C. for 30 seconds; 60° C. for 30 seconds; 72° C. for 1 minute]×35 cycles: PCR amplification 72° C. for 10 minutes: final elongation reaction The nucleotide sequences of the forward and reverse primers used for RT-PCR are as shown below.

Forward primer: 5'-GCTCAGGTCGGATTGACATT-3' (SEQ ID NO: 1)

Reverse primer: 5'-GGGCAACTCTTCCACCAGTA-3' (SEQ ID NO: 2)

The above PCR reaction product (1 μL) was analyzed using a Bioanalyzer (Agilent) and a MultiNA system (Shimadzu Corporation, Japan).

The polynucleotide level "A" in the band with exon 45 skipping and the polynucleotide level "B" in the band without exon 45 skipping were measured. Based on these measured values of "A" and "B," the skipping efficiency was determined according to the following equation.

Skipping efficiency (%)=$A/(A+B) \times 100$

Experimental Results

The results obtained are shown in FIGS. 1 to 5, 8, 10, 11 and 16 to 24. This experiment indicated that the oligomer of the present invention effectively caused exon 45 skipping.

Test Example 2

In Vitro Assay

The same procedures as shown in Test Example 1 were repeated to conduct this experiment, except that $3.5 \times 10^5$ RD cells (human rhabdomyosarcoma cell line) were transfected with the oligomer of the present invention alone (PMO No. 11 or PMO No. 9) or with either of the two unit oligomers constituting the oligomer of the present invention or with a mixture thereof at a concentration of 3 μM through Nucleofector II (Lonza) using an Amaxa Cell Line Nucleofector Kit L. The program used was T-030. Combinations of the sequences transfected are as shown below.

TABLE 7

Combinations of the sequences transfected

| Sequence combination | Transfection concentration (μM) |
|---|---|
| PMO No. 11 (PMO No. 27 and PMO No. 28 connected together) | 3 μM |
| PMO No. 27 | 3 μM |
| PMO No. 28 | 3 μM |
| PMO No. 27 and PMO No. 28 | 3 μM each |
| PMO No. 9 (PMO No. 25 and PMO No. 26 connected together) | 3 μM |
| PMO No. 25 | 3 μM |
| PMO No. 26 | 3 μM |
| PMO No. 25 and PMO No. 26 | 3 μM each |
| PMO No. 72 (PMO No. 82 and PMO No. 83 connected together) | 3 μM |
| PMO No. 82 | 3 μM |
| PMO No. 83 | 3 μM |
| PMO No. 82 and PMO No. 83 | 3 μM each |

Experimental Results

Figure 6:
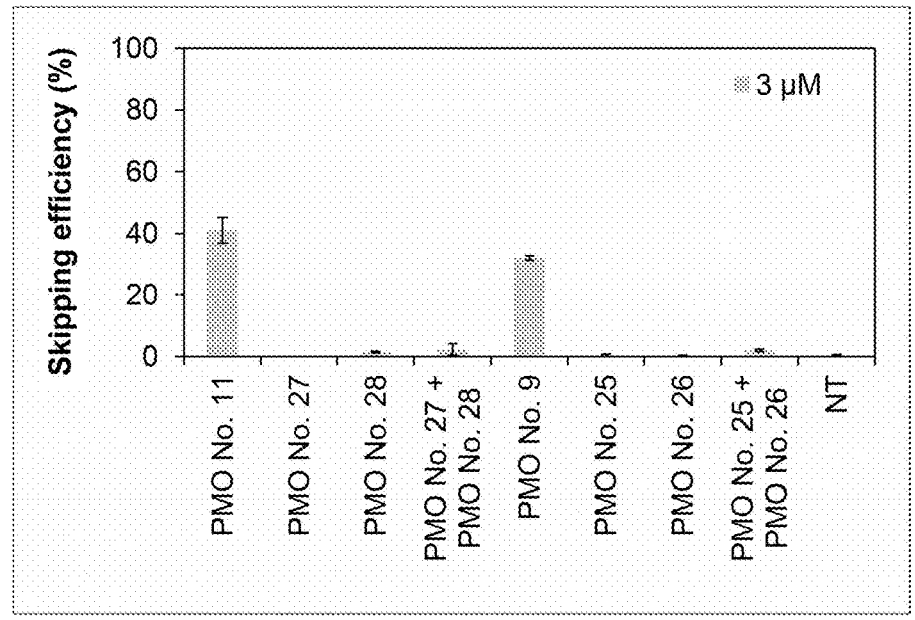
FIG. 6 is a graph showing the efficiency of exon 45 skipping in the human dystrophin gene in human rhabdomyosarcoma cells (RD cells).
Figure 7:
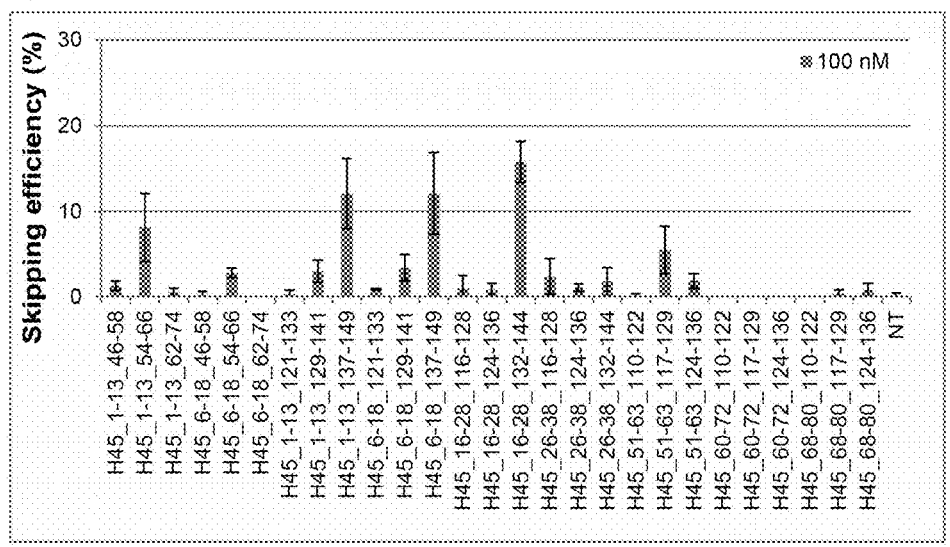
FIG. 7 is a graph showing the efficiency of exon 45 skipping in the human dystrophin gene in human rhabdomyosarcoma cells (RD cells).
Figure 8:
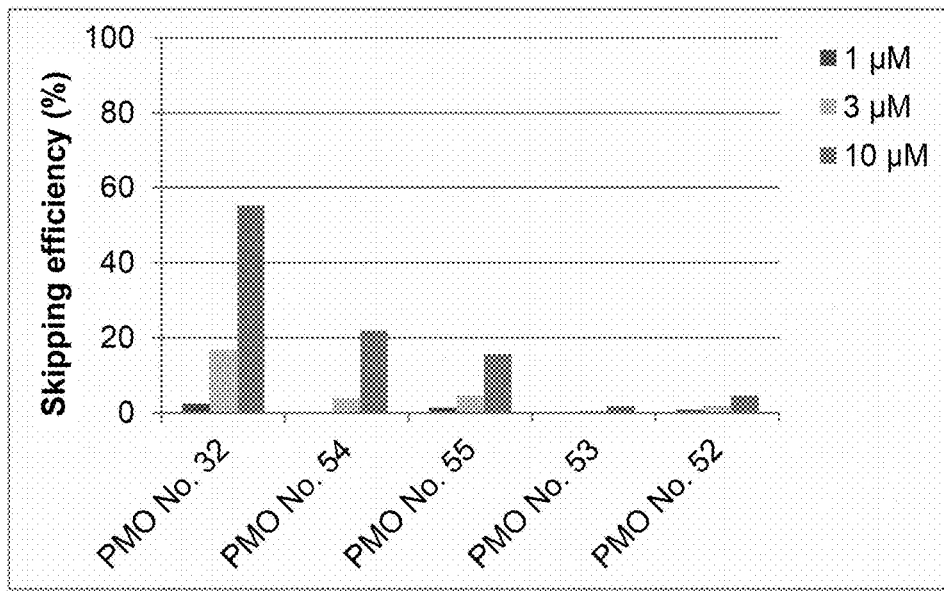
FIG. 8 is a graph showing the efficiency of exon 45 skipping in the human dystrophin gene in human rhabdomyosarcoma cells (RD cells).
Figure 25:
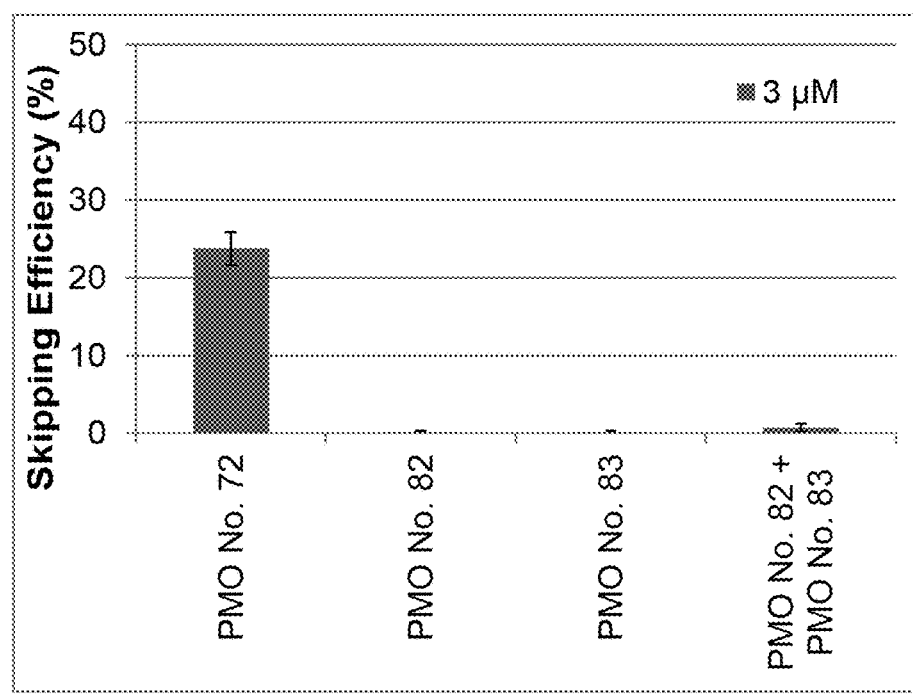
FIG. 25 is a graph showing the efficiency of exon 45 skipping in the human dystrophin gene in human rhabdomyosarcoma cells (RD cells).

The results obtained are shown in FIGS. 6 and 25. This experiment indicated that the oligomer of the present invention, i.e., PMO No. 11 (SEQ ID NO: 10), PMO No. 9 (SEQ ID NO: 8) or PMO No. 72 (SEQ ID NO: 79), each being consisting of connected two antisense oligomers targeting different sites in exon 45, caused exon 45 skipping with higher efficiency when compared to the respective antisense oligomers constituting each oligomer (i.e., PMO No. 27 (SEQ ID NO: 36), PMO No. 28 (SEQ ID NO: 37), PMO No. 25 (SEQ ID NO: 34), PMO No. 26 (SEQ ID NO: 35), PMO No. 82 (SEQ ID NO: 144) or PMO No. 83 (SEQ ID NO: 145)) or a mixture thereof (i.e., PMO No. 27 and PMO No. 28, PMO No. 25 and PMO No. 26, or PMO No. 82 and PMO No. 83).

Test Example 3

In Vitro Assay

This experiment was conducted by using the antisense oligomers in 2'-O-methoxy-phosphorothioate form (2'-OMe-S-RNA) shown in SEQ ID NOs: 89 to 141, 11 and 12. These various antisense oligomers used for assay were purchased from Japan Bio Services Co., Ltd. The sequences of these various antisense oligomers are shown below.

| Sequence name | Nucleotide sequence | SEQ ID NO: |
|---|---|---|
| [TABLE 8-1] | | |
| H45_1-15_48-62 | UCCCCAGUUGCAUUCGCCAUCCUGGAGUUC | 89 |
| H45_1-15_56-70 | UUAUUUCUUCCCCAGGCCAUCCUGGAGUUC | 90 |
| H45_1-15_131-145 | CCUCCUGCCACCGCAGCCAUCCUGGAGUUC | 91 |
| H45_-2-13_131-145 | CCUCCUGCCACCGCACAUCCUGGAGUUCCU | 92 |
| H45_-2-13_135-149 | CAGACCUCCUGCCACCAUCCUGGAGUUCCU | 93 |
| H45_-2-13_48-62 | UCCCCAGUUGCAUUCCAUCCUGGAGUUCCU | 94 |
| H45_-2-13_52-66 | UUCUUCCCCAGUUGCCAUCCUGGAGUUCCU | 95 |
| H45_-2-13_56-70 | UUAUUUCUUCCCCAGCAUCCUGGAGUUCCU | 96 |
| H45_-2-13_18-32 | GUUUGCCGCUGCCCACAUCCUGGAGUUCCU | 97 |
| H45_-2-13_139-153 | UUUGCAGACCUCCUGCAUCCUGGAGUUCCU | 98 |
| H45_1-17_135-147 | GACCUCCUGCCACAUGCCAUCCUGGAGUUC | 99 |
| H45_1-17_52-64 | CUUCCCCAGUUGCAUGCCAUCCUGGAGUUC | 100 |
| H45_1-15_139-153 | UUUGCAGACCUCCUGGCCAUCCUGGAGUUC | 101 |
| H45_-2-13_99-113 | UUUUCCUGUAGAAUACAUCCUGGAGUUCCU | 102 |
| H45_53-67_132-146 | ACCUCCUGCCACCGCUUUCUUCCCCAGUUG | 103 |
| H45_16-30_99-113 | UUUUCCUGUAGAAUAUUGCCGCUGCCCAAU | 104 |
| H45_1-15_153-167 | CUGUCUGACAGCUGUGCCAUCCUGGAGUUC | 105 |
| H45_1-15_67-81 | GGAUUGCUGAAUUAUGCCAUCCUGGAGUUC | 106 |
| H45_1-15_99-113 | UUUUCCUGUAGAAUAGCCAUCCUGGAGUUC | 107 |
| H45_1-13_46-58 | CAGUUGCAUUCAACAUCCUGGAGUUC | 108 |
| H45_1-13_54-66 | UUCUUCCCCAGUUCAUCCUGGAGUUC | 109 |
| H45_1-13_62-74 | UGAAUUAUUUCUUCACCUGGAGUUC | 110 |
| H45_6-18_46-58 | CAGUUGCAUUCAAAAUGCCAUCCUGG | 111 |
| H45_6-18_54-66 | UUCUUCCCCAGUUAAUGCCAUCCUGG | 112 |
| H45_6-18_62-74 | UGAAUUAUUUCUUAAUGCCAUCCUGG | 113 |
| H45_1-13_121-133 | GCAGAUUCAGGCUCAUCCUGGAGUUC | 114 |
| H45_1-13_129-141 | CUGCCACCGCAGACAUCCUGGAGUUC | 115 |
| H45_1-13_137-149 | CAGACCUCCUGCCCAUCCUGGAGUUC | 116 |
| H45_6-18_121-133 | GCAGAUUCAGGCUAAUGCCAUCCUGG | 117 |
| H45_6-18_129-141 | CUGCCACCGCAGAAAUGCCAUCCUGG | 118 |
| H45_6-18_137-149 | CAGACCUCCUGCCAAUGCCAUCCUGG | 142 |
| H45_16-28_116-128 | UUCAGGCUUCCCAGCCGCUGCCCAAU | 119 |
| H45_16-28_124-136 | ACCGCAGAUUCAGGCCGCUGCCCAAU | 120 |
| [TABLE 8-2] | | |
| H45_16-28_132-144 | CUCCUGCCACCGCGCCGCUGCCCAAU | 121 |
| H45_26-38_116-128 | UUCAGGCUUCCCAACAACAGUUUGCC | 122 |
| H45_26-38_124-136 | ACCGCAGAUUCAGACAACAGUUUGCC | 123 |
| H45_26-38_132-144 | CUCCUGCCACCGCACAACAGUUUGCC | 124 |
| H45_51-63_110-122 | CUUCCCAAUUUUUUCCCCAGUUGCA | 125 |
| H45_51-63_117-129 | AUUCAGGCUUCCCUUCCCCAGUUGCA | 126 |
| H45_51-63_124-136 | ACCGCAGAUUCAGUUCCCCAGUUGCA | 127 |
| H45_60-72_110-122 | CUUCCCAAUUUUUAAUUAUUUCUUCC | 128 |
| H45_60-72_117-129 | AUUCAGGCUUCCCAAUUAUUUCUUCC | 129 |
| H45_60-72_124-136 | ACCGCAGAUUCAGAAUUAUUUCUUCC | 130 |
| H45_68-80_110-122 | CUUCCCAAUUUUUGAUUGCUGAAUUA | 131 |

-continued

| Sequence name | Nucleotide sequence | SEQ ID NO: |
|---|---|---|
| H45_68-80_117-129 | AUUCAGGCUUCCCGAUUGCUGAAUUA | 132 |
| H45_68-80_124-136 | ACCGCAGAUUCAGGAUUGCUGAAUUA | 133 |
| H45_-10-5_52-66 | UUCUUCCCCAGUUGCAGUUCCUGUAAGAUA | 134 |
| H45_-10-5_135-149 | CAGACCUCCUGCCACAGUUCCUGUAAGAUA | 135 |
| H45_69-83_95-109 | CCUGUAGAAUACUGGGAGGAUUGCUGAAUU | 136 |
| H45_16-30_84-98 | CUGGCAUCUGUUUUUUUGCCGCUGCCCAAU | 137 |
| H45_16-30_53-67 | UUUCUUCCCCAGUUGUUGCCGCUGCCCAAU | 138 |
| H45_1-15_84-98 | CUGGCAUCUGUUUUUGCCAUCCUGGAGUUC | 139 |
| H45_84-98_132-146 | ACCUCCUGCCACCGCCUGGCAUCUGUUUUU | 140 |
| H45_53-67_99-113 | UUUUCCUGUAGAAUAUUUCUUCCCCAGUUG | 141 |
| H45_1-15_-52-66 | UUCUUCCCCAGUUGCGCCAUCCUGGAGUUC | 11 |
| H45_1-15_135-149 | CAGACCUCCUGCCACGCCAUCCUGGAGUUC | 12 |

In 24-well plates, 5×10⁴ RD cells (human rhabdomyosarcoma cell line) were seeded per well and cultured overnight at 37° C. under 5% $CO_2$ conditions in 0.5 mL of Eagle's minimal essential medium (EMEM) (SIGMA; the same applies hereinafter) containing 10% fetal calf serum (FCS) (Invitrogen). The above various antisense oligomers for exon 45 skipping (Japan Bio Services Co., Ltd., Japan) (1 μM or 300 nM) were formed into conjugates with Lipofectamine 2000 (Invitrogen), and each conjugate was added to the RD cells, which had been replaced in 0.45 mL fresh medium, in a volume of 50 μL per well to give a final concentration of 100 nM or 30 nM.

After addition, the cells were cultured overnight. After the cells were washed once with PBS (Nissui Pharmaceutical Co., Ltd., Japan; the same applies hereinafter), 350 μL of Buffer RLT (QIAGEN) containing 1% 2-mercaptoethanol (Nacalai Tesque, Inc., Japan) was added to the cells, and the cells were lysed by being allowed to stand at room temperature for a few minutes. The cell lysate was collected into a QIAshredder homogenizer (QIAGEN) and centrifuged at 15,000 rpm for 2 minutes to prepare a homogenate. The total RNA was extracted in accordance with the protocol attached to an RNeasy Mini Kit (QIAGEN). The concentration of the extracted total RNA was measured with a NanoDrop ND-1000 spectrophotometer (LMS Co., Ltd., Japan).

One-Step RT-PCR was performed on 400 ng of the extracted total RNA using a QIAGEN OneStep RT-PCR Kit (QIAGEN). A reaction solution was prepared in accordance with the protocol attached to the kit. The thermal cycler used was PTC-100 (MJ Research) or TaKaRa PCR Thermal Cycler Dice Touch (Takara Bio Inc., Japan). The RT-PCR program used is as shown below.

50° C. for 30 minutes: reverse transcription reaction
95° C. for 15 minutes: polymerase activation, reverse transcriptase inactivation, cDNA thermal denaturation
[94° C. for 30 seconds; 60° C. for 30 seconds; 72° C. for 1 minute]×35 cycles: PCR amplification
72° C. for 10 minutes: final elongation reaction The nucleotide sequences of the forward and reverse primers used for RT-PCR are as shown below.

```
                                     (SEQ ID NO: 1)
Forward primer: 5'-GCTCAGGTCGGATTGACATT-3'

(SEQ ID NO: 2)
Reverse primer: 5'-GGGCAACTCTTCCACCAGTA-3'
```

The above PCR reaction product (1 μL) was analyzed by a Bioanalyzer (Agilent) and a MultiNA system (Shimadzu Corporation, Japan).

The polynucleotide level "A" in the band with exon 45 skipping and the polynucleotide level "B" in the band without exon 45 skipping were measured. Based on these measured values of "A" and "B," the skipping efficiency was determined according to the following equation.

Skipping efficiency (%)=$A/(A+B)\times 100$

Experimental Results

The results obtained are shown in FIGS. 7 and 12 to 15. This experiment indicated that the antisense oligomer of the present invention effectively caused exon 45 skipping.

Test Example 4

In Vitro Assay

The same procedures as shown in Test Example 1 were repeated to conduct this experiment, except that 3.5×10⁵ RD cells (human rhabdomyosarcoma cell line) were transfected with the oligomer of the present invention alone (PMO No. 2, PMO No. 31 or PMO No. 32) or with either of the two unit oligomers constituting the oligomer of the present invention at a concentration of 3 μM or 10 μM through Nucleofector II (Lonza) using an Amaxa Cell Line Nucleofector Kit L. The program used was T-030. Combinations of the sequences transfected are as shown below.

TABLE 9

| Sequence | Transfection concentration |
|---|---|
| PMO No. 2 | 3 μM or 10 μM |
| (PMO No. 66 and PMO No. 67 connected together) | |
| PMO NO. 66 | 3 μM or 10 μM |
| PMO No. 67 | 3 μM or 10 μM |
| PMO No. 31 | 3 μM or 10 μM |
| (PMO No. 63 and PMO No. 64 connected together) | |
| PMO No. 63 | 3 μM or 10 μM |
| PMO No. 64 | 3 μM or 10 μM |
| PMO No. 32 | 3 μM or 10 μM |
| (PMO No. 63 and PMO No. 65 connected together) | |
| PMO No. 65 | 3 μM or 10 μM |

Experimental Results

Figure 9:
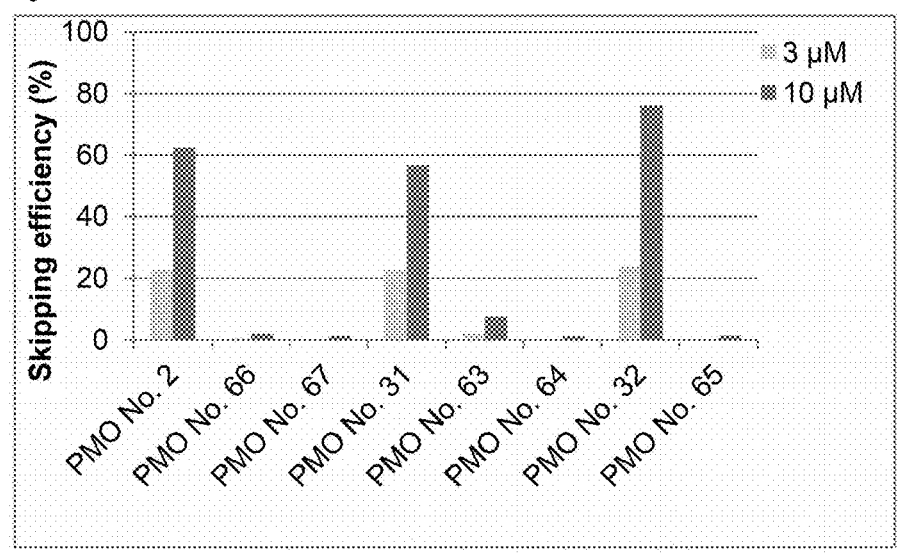
FIG. 9 is a graph showing the efficiency of exon 45 skipping in the human dystrophin gene in human rhabdomyosarcoma cells (RD cells).
Figure 10:
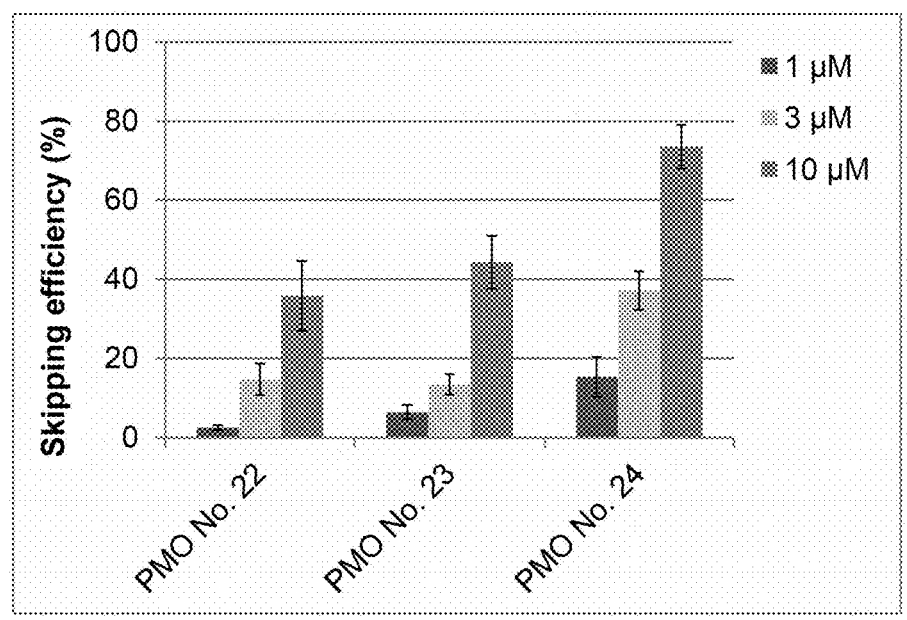
FIG. 10 is a graph showing the efficiency of exon 45 skipping in the human dystrophin gene in human rhabdomyosarcoma cells (RD cells).
Figure 11:
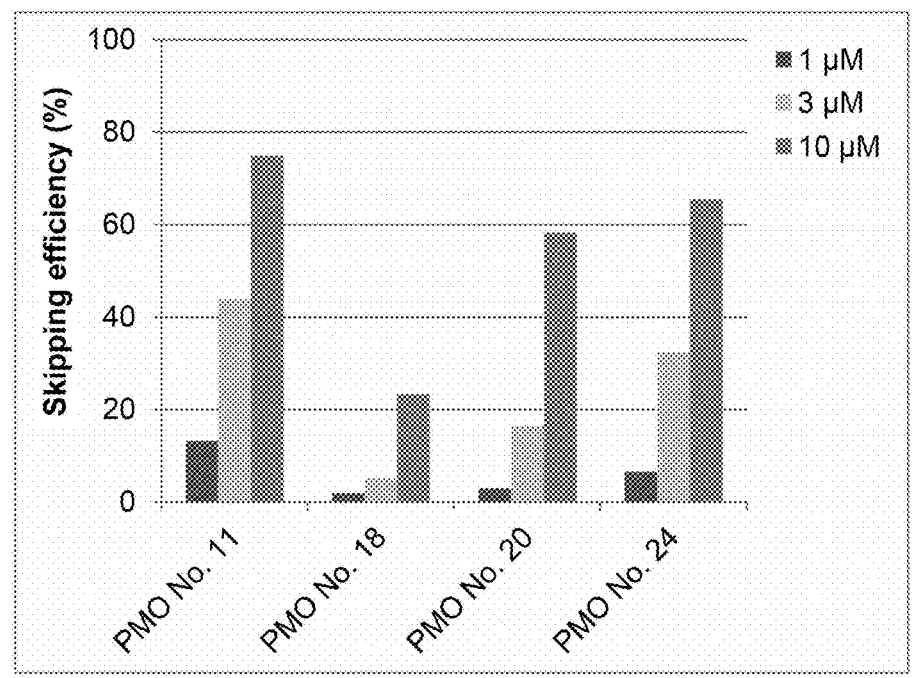
FIG. 11 is a graph showing the efficiency of exon 45 skipping in the human dystrophin gene in human rhabdomyosarcoma cells (RD cells).
Figure 12:
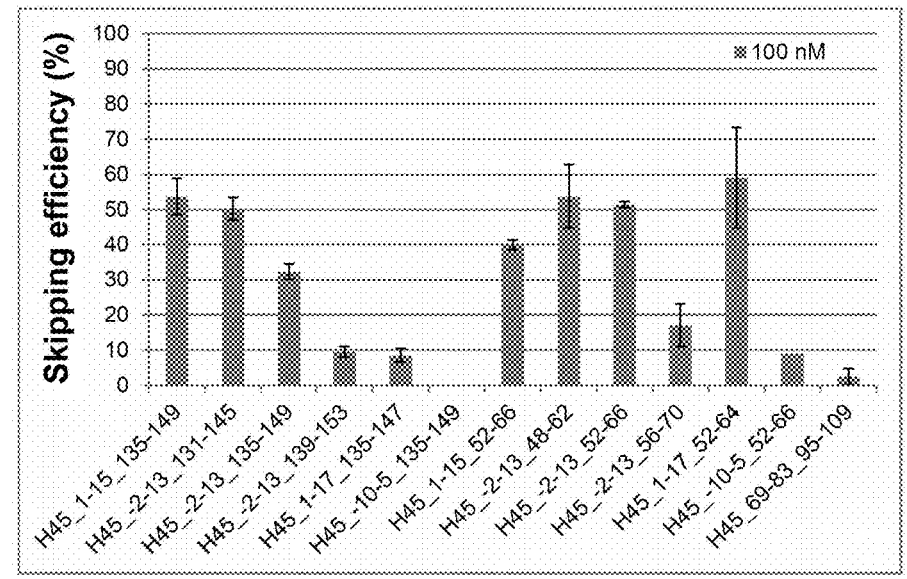
FIG. 12 is a graph showing the efficiency of exon 45 skipping in the human dystrophin gene in human rhabdomyosarcoma cells (RD cells).
Figure 13:
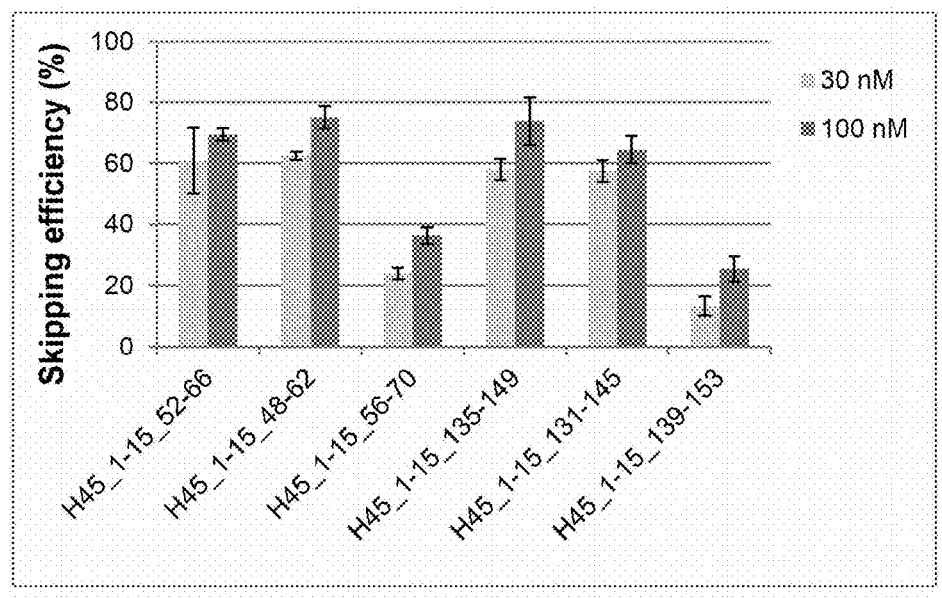
FIG. 13 is a graph showing the efficiency of exon 45 skipping in the human dystrophin gene in human rhabdomyosarcoma cells (RD cells).
Figure 14:
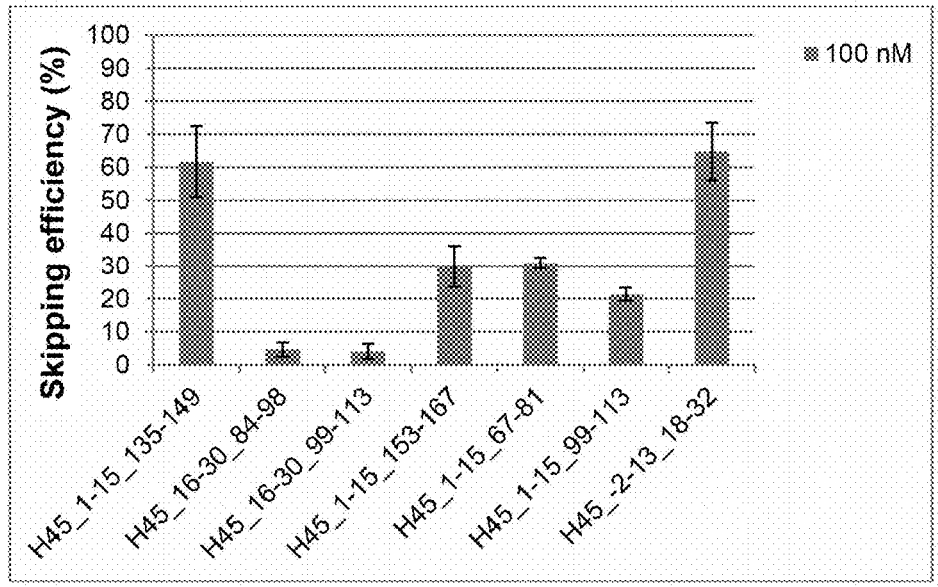
FIG. 14 is a graph showing the efficiency of exon 45 skipping in the human dystrophin gene in human rhabdomyosarcoma cells (RD cells).
Figure 15:
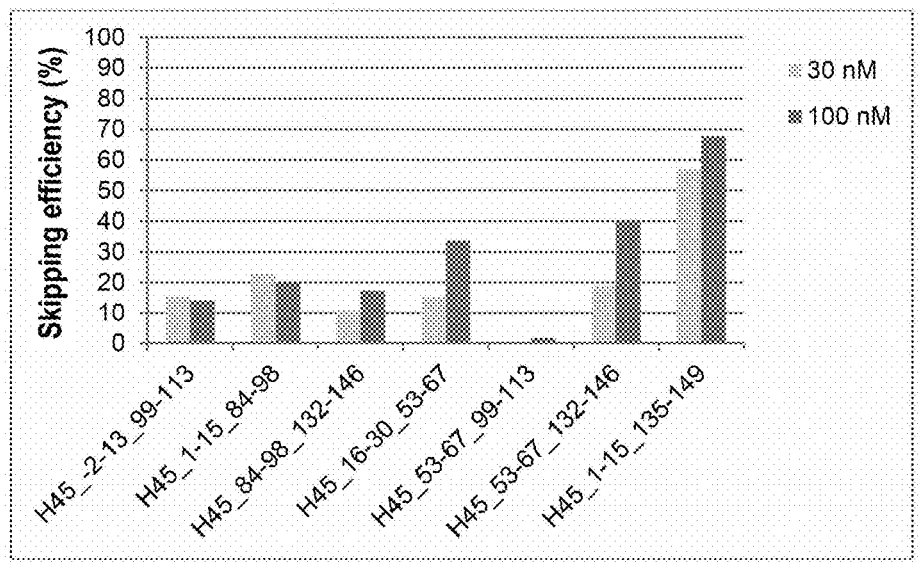
FIG. 15 is a graph showing the efficiency of exon 45 skipping in the human dystrophin gene in human rhabdomyosarcoma cells (RD cells).
Figure 16:
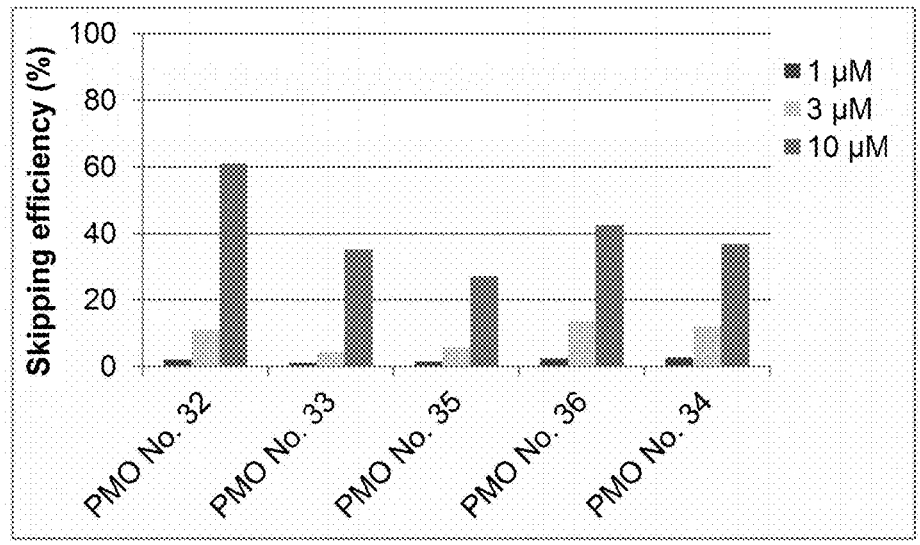
FIG. 16 is a graph showing the efficiency of exon 45 skipping in the human dystrophin gene in human rhabdomyosarcoma cells (RD cells).
Figure 17:
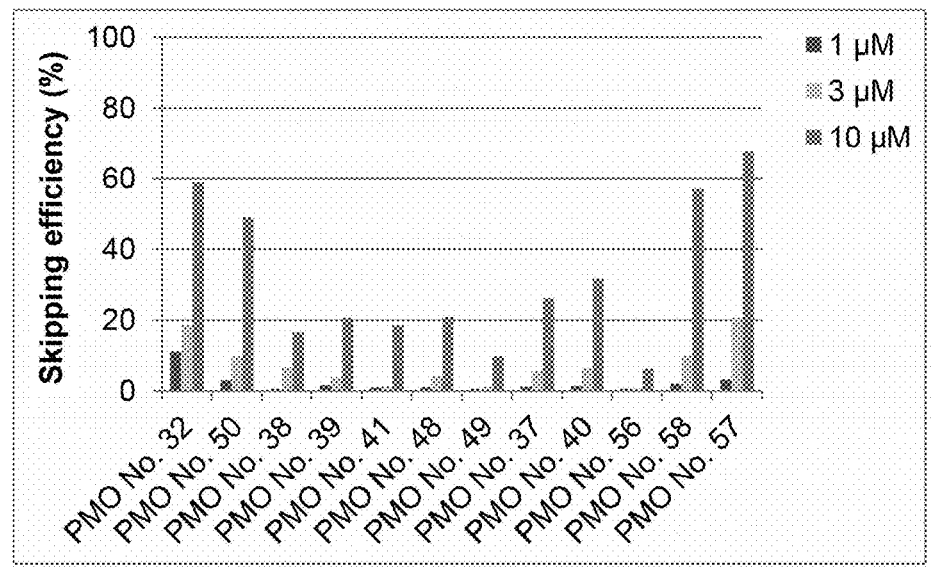
FIG. 17 is a graph showing the efficiency of exon 45 skipping in the human dystrophin gene in human rhabdomyosarcoma cells (RD cells).
Figure 18:
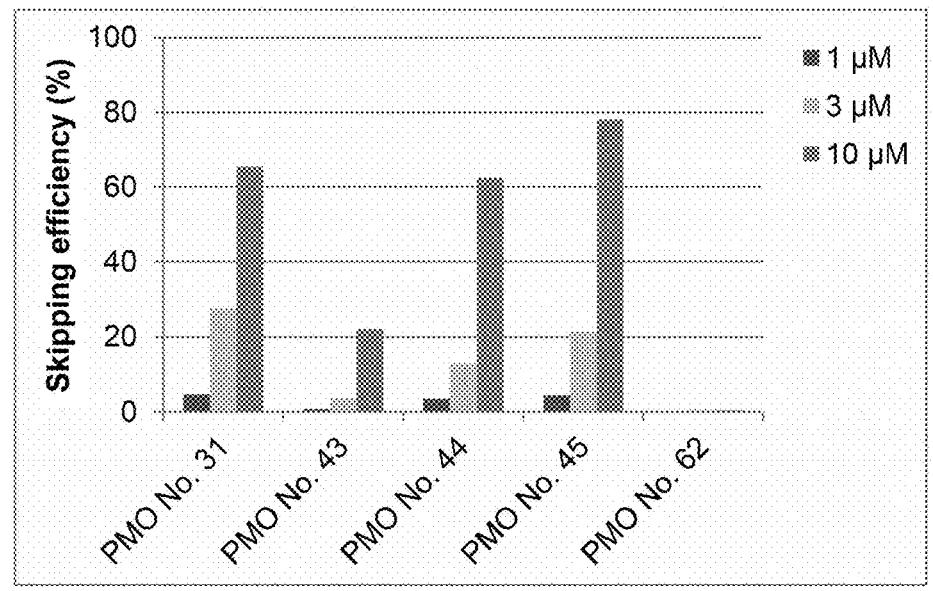
FIG. 18 is a graph showing the efficiency of exon 45 skipping in the human dystrophin gene in human rhabdomyosarcoma cells (RD cells).
Figure 19:
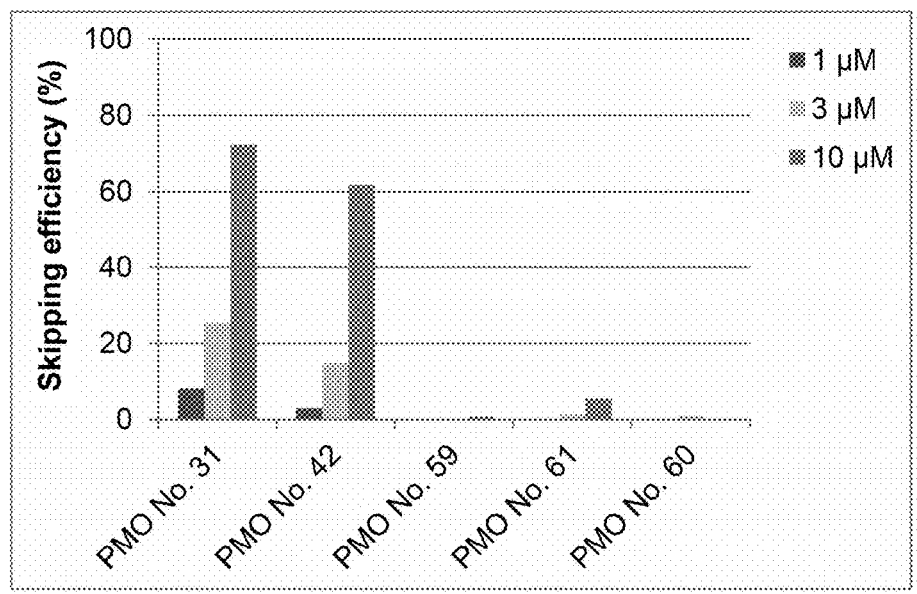
FIG. 19 is a graph showing the efficiency of exon 45 skipping in the human dystrophin gene in human rhabdomyosarcoma cells (RD cells).
Figure 20:
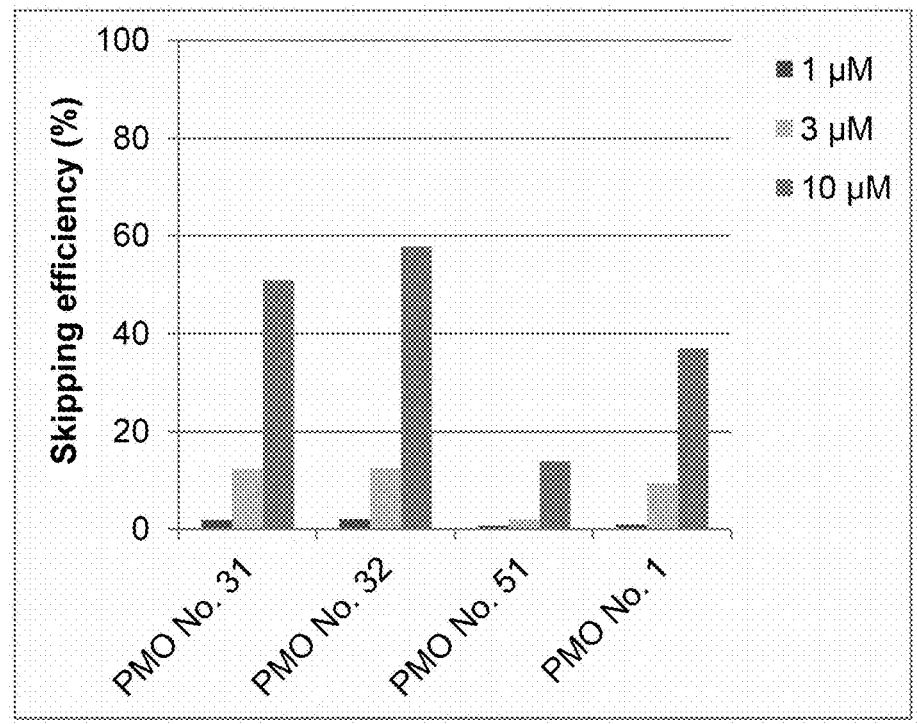
FIG. 20 is a graph showing the efficiency of exon 45 skipping in the human dystrophin gene in human rhabdomyosarcoma cells (RD cells).
Figure 21:
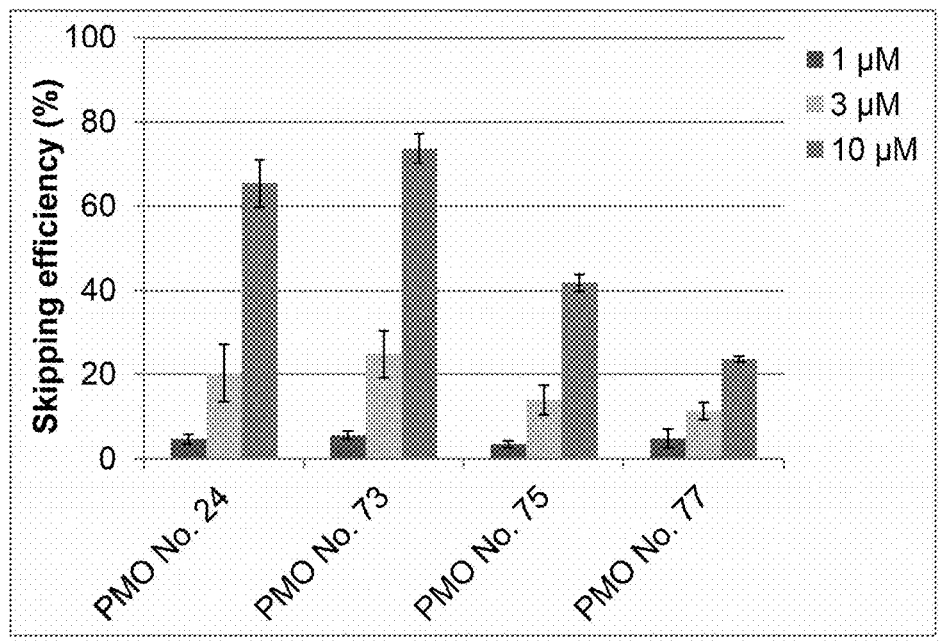
FIG. 21 is a graph showing the efficiency of exon 45 skipping in the human dystrophin gene in human rhabdomyosarcoma cells (RD cells).
Figure 22:
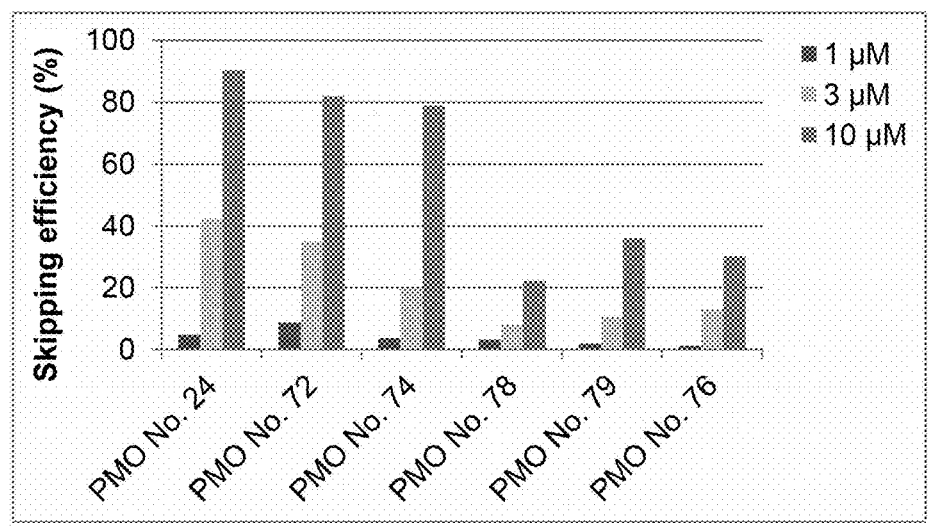
FIG. 22 is a graph showing the efficiency of exon 45 skipping in the human dystrophin gene in human rhabdomyosarcoma cells (RD cells).
Figure 23:
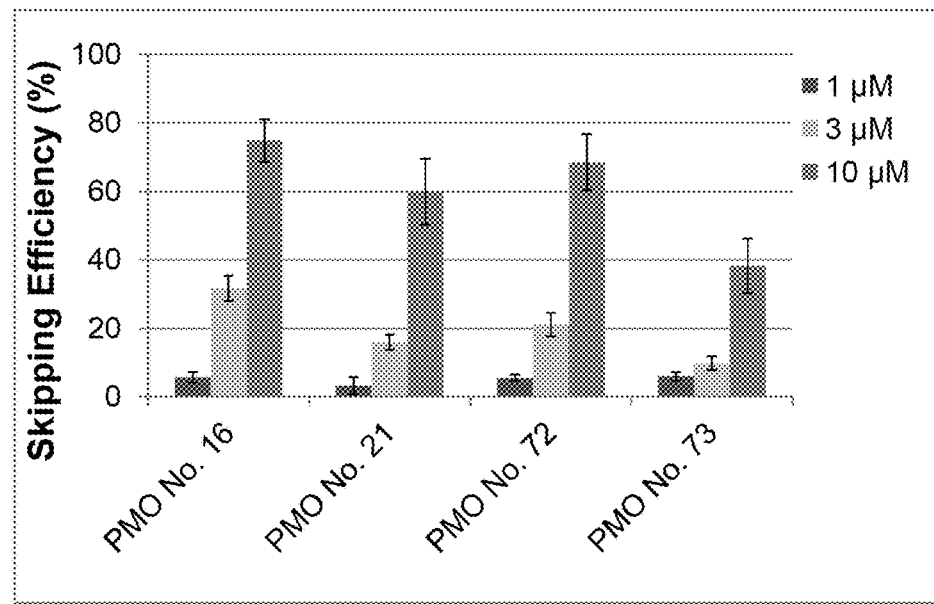
FIG. 23 is a graph showing the efficiency of exon 45 skipping in the human dystrophin gene in human rhabdomyosarcoma cells (RD cells).
Figure 24:
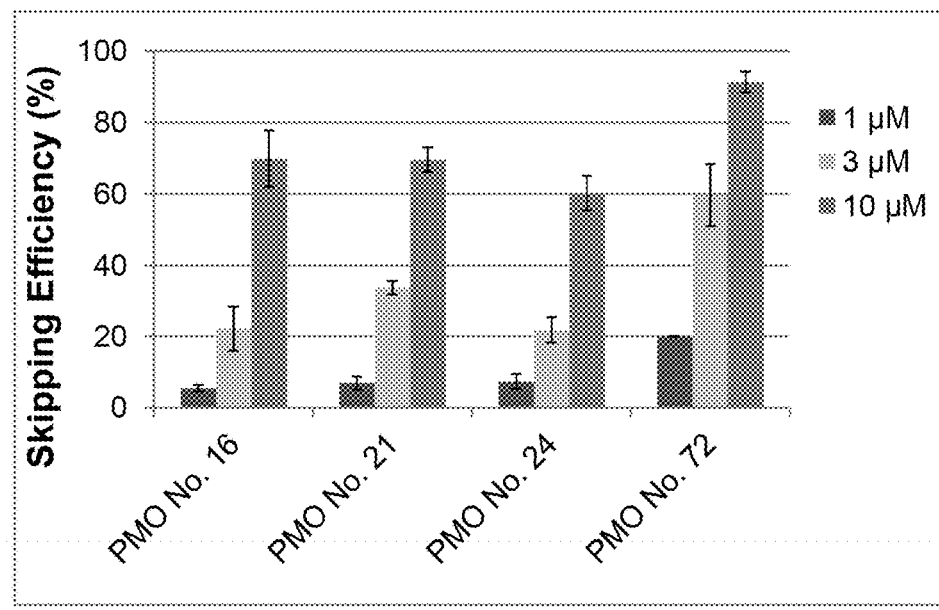
FIG. 24 is a graph showing the efficiency of exon 45 skipping in the human dystrophin gene in human rhabdomyosarcoma cells (RD cells).

The results obtained are shown in FIG. 9. This experiment indicated that the oligomer of the present invention, i.e., PMO No. 2 (SEQ ID NO: 7), PMO No. 31 (SEQ ID NO: 11)

and PMO No. 32 (SEQ ID NO: 12), each being consisting of connected two antisense nucleic acids targeting different sites in exon 45, caused exon 45 skipping with higher efficiency when compared to the respective antisense nucleic acids constituting each oligomer (i.e., PMO No. 66, PMO No. 63, PMO No. 64 or PMO No. 65).

INDUSTRIAL APPLICABILITY

As can be seen from the experimental results shown in the test examples, the oligomer of the present invention consisting of short oligomers connected together was found to cause exon 45 skipping in RD cells. Thus, the oligomer of the present invention is very useful in the treatment of DMD.

The invention claimed is:

1. An antisense oligomer consisting of a nucleotide sequence selected from the group consisting of SEQ ID NOs: 25, 30, 33, 79, and 80, or pharmaceutically acceptable salt or hydrate thereof,
   wherein the antisense oligomer is a morpholino oligomer, a peptide nucleic acid (PNA), or an oligonucleotide comprising at least one nucleotide having:
   (i) a modified sugar moiety, wherein the 2'-OH group of a ribose is replaced by any one selected from the group consisting of R, R'OR, SH, SR, $NH_2$, NHR, $NR_2$, $N_3$, CN, F, Cl, Br and I (wherein R is an alkyl or an aryl and R' is an alkylene), or
   (ii) a modified phosphate-binding region selected from the group consisting of a phosphorothioate bond, a phosphorodithioate bond, an alkylphosphonate bond, a phosphoramidate bond, and a boranophosphate bond.

2. The antisense oligomer, or pharmaceutically acceptable salt or hydrate thereof according to claim 1, wherein the antisense oligomer consists of the nucleotide sequence of SEQ ID NO: 25.

3. The antisense oligomer, or pharmaceutically acceptable salt or hydrate thereof according to claim 1, wherein the antisense oligomer consists of the nucleotide sequence of SEQ ID NO: 30.

4. The antisense oligomer, or pharmaceutically acceptable salt or hydrate thereof according to claim 1, wherein the antisense oligomer consists of the nucleotide sequence of SEQ ID NO: 33.

5. The antisense oligomer, or pharmaceutically acceptable salt or hydrate thereof according to claim 1, wherein the antisense oligomer consists of the nucleotide sequence of SEQ ID NO: 79.

6. The antisense oligomer, or pharmaceutically acceptable salt or hydrate thereof according to claim 1, wherein the antisense oligomer consists of the nucleotide sequence of SEQ ID NO: 80.

7. The antisense oligomer, or pharmaceutically acceptable salt or hydrate thereof according to claim 1, which is a phosphorodiamidate morpholino oligomer, or pharmaceutically acceptable salt or hydrate thereof.

8. The antisense oligomer, or pharmaceutically acceptable salt or hydrate thereof according to claim 1, wherein the antisense oligomer is a morpholino oligomer or phosphorodiamidate morpholino oligomer, and wherein the 5'-terminal end of the antisense oligomer is any one of the groups represented by chemical formulae (1) to (3) shown below, or pharmaceutically acceptable salt or hydrate thereof,

[Formula 25]

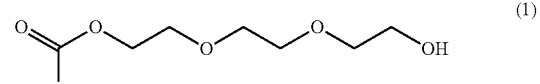

(1)

(2)

-continued

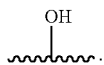 (3)

9. A pharmaceutical composition for treatment of muscular dystrophy, which comprises an antisense oligomer consisting of any one nucleotide sequence selected from the group consisting of SEQ ID NOs: 25, 30, 33, 79, and 80, or pharmaceutically acceptable salt or hydrate thereof as an active ingredient.

10. The pharmaceutical composition according to claim 9, further comprising a pharmaceutically acceptable carrier.

11. A method for treating muscular dystrophy, comprising the step of administering a muscular dystrophy patient with an antisense oligomer consisting of a nucleotide sequence selected from the group consisting of SEQ ID NOs: 25, 30, 33, 79, and 80, or pharmaceutically acceptable salt or hydrate thereof.

12. The method for treating muscular dystrophy according to claim 11, wherein the muscular dystrophy patient has a mutation to be targeted by exon 45 skipping in the dystrophin gene.

13. The method for treating muscular dystrophy according to claim 11, wherein the muscular dystrophy patient is a human patient.

14. A method for treating muscular dystrophy, comprising the step of administering a muscular dystrophy patient with the pharmaceutical composition according to claim 9.

15. The method for treating muscular dystrophy according to claim 14, wherein the muscular dystrophy patient has a mutation to be targeted by exon 45 skipping in the dystrophin gene.

16. The method for treating muscular dystrophy according to claim 14, wherein the muscular dystrophy patient is a human patient.

17. A method for treating muscular dystrophy, comprising the step of administering a muscular dystrophy patient with the pharmaceutical composition according to claim 10.

18. The method for treating muscular dystrophy according to claim 17, wherein the muscular dystrophy patient has a mutation to be targeted by exon 45 skipping in the dystrophin gene.

19. The method for treating muscular dystrophy according to claim 17, wherein the muscular dystrophy patient is a human patient.

* * * * *